US010729386B2

United States Patent
Lipman et al.

(10) Patent No.: US 10,729,386 B2
(45) Date of Patent: Aug. 4, 2020

(54) ANALYTE MONITORING SYSTEM WITH AUDIBLE FEEDBACK

(71) Applicant: Intuity Medical, Inc., Sunnyvale, CA (US)

(72) Inventors: Kelley J. Lipman, Livermore, CA (US); Robin S. Gaffney, Redwood City, CA (US); Raul Escutia, Sunnyvale, CA (US); Matthew M. Shemluck, San Francisco, CA (US); Paul D. Reynolds, Palo Alto, CA (US)

(73) Assignee: Intuity Medical, Inc., Fremont, CA (US)

( * ) Notice: Subject to any disclaimer, the term of this patent is extended or adjusted under 35 U.S.C. 154(b) by 0 days.

(21) Appl. No.: 14/311,114

(22) Filed: Jun. 20, 2014

(65) Prior Publication Data

US 2014/0376762 A1    Dec. 25, 2014

Related U.S. Application Data

(60) Provisional application No. 61/838,171, filed on Jun. 21, 2013.

(51) Int. Cl.
*A61B 5/00* (2006.01)
*A61B 5/151* (2006.01)
(Continued)

(52) U.S. Cl.
CPC ........ *A61B 5/7405* (2013.01); *A61B 5/14532* (2013.01); *A61B 5/14546* (2013.01);
(Continued)

(58) Field of Classification Search
CPC .............. A61B 5/7405; A61B 5/15117; A61B 5/15113; A61B 5/157; A61B 5/15163;
(Continued)

(56) References Cited

U.S. PATENT DOCUMENTS

| 842,690 A | 1/1907 | Oswalt |
| D137,874 S | 5/1944 | Partridge |

(Continued)

FOREIGN PATENT DOCUMENTS

| CA | 2 201 530 A1 | 9/1997 |
| CA | 2 513 465 A1 | 8/2004 |

(Continued)

OTHER PUBLICATIONS

ADA Consensus Development Panel. (Jan.-Feb. 1987). "Consensus Statement on Self-Monitoring of Blood Glucose," *Diabetes Care* 10(1):95-99.

(Continued)

*Primary Examiner* — Samuel P Siefke
(74) *Attorney, Agent, or Firm* — Cooley LLP

(57) ABSTRACT

Described here are devices, systems, and methods for analyte measurement. The analyte measurement devices and systems may be configured to produce a prompt that may convey information, instructions and/or encouragement to a user. In some variations, analyte measurement devices may be configured to change a prompt based on the replacement or addition of components of/to the device. In some instances, a prompt may be an auditory prompt and/or a visual prompt. In some variations, a system may comprise an analyte measurement device comprising a housing, a speaker, and a control unit. The housing may comprise a releasable housing portion comprising an identifier that is associated with a prompt. In some variations, a system may comprise an analyte measurement device and a skin that may releasably attach to the analyte measurement device and may comprise an identifier that is associated with a prompt.

32 Claims, 10 Drawing Sheets

(51) Int. Cl.
*A61B 5/157* (2006.01)
*A61B 5/15* (2006.01)
*A61B 90/98* (2016.01)
*A61B 5/145* (2006.01)
*H04R 1/02* (2006.01)

(52) U.S. Cl.
CPC ........ *A61B 5/157* (2013.01); *A61B 5/150022* (2013.01); *A61B 5/15113* (2013.01); *A61B 5/15117* (2013.01); *A61B 5/15153* (2013.01); *A61B 5/15163* (2013.01); *A61B 5/150389* (2013.01); *A61B 5/150503* (2013.01); *A61B 5/150793* (2013.01); *A61B 5/150801* (2013.01); *A61B 5/150854* (2013.01); *A61B 5/4845* (2013.01); *A61B 90/98* (2016.02); *A61B 5/742* (2013.01); *A61B 2560/029* (2013.01); *A61B 2560/0406* (2013.01); *A61B 2560/0431* (2013.01); *A61B 2560/0443* (2013.01); *A61B 2562/08* (2013.01); *H04R 1/028* (2013.01)

(58) Field of Classification Search
CPC .......... A61B 5/15153; A61B 5/150022; A61B 5/150389; A61B 5/150793; A61B 5/150503; A61B 5/150854; A61B 5/150801; A61B 90/98; A61B 5/14532; A61B 5/14546; A61B 5/4845; A61B 2560/0406; A61B 2562/08; A61B 2560/0431; A61B 2560/0443; A61B 2560/029; A61B 5/742; H04R 1/028
See application file for complete search history.

(56) References Cited

U.S. PATENT DOCUMENTS

| | | | |
|---|---|---|---|
| 2,749,797 A | 3/1950 | Harks | |
| 3,092,465 A | 6/1963 | Adams, Jr. | |
| 3,310,002 A | 3/1967 | Wilburn | |
| 3,620,209 A | 11/1971 | Kravitz | |
| 3,623,475 A | 11/1971 | Sanz et al. | |
| 3,626,929 A | 12/1971 | Sanz et al. | |
| 3,630,957 A | 12/1971 | Rey | |
| D223,165 S | 3/1972 | Komendat | |
| 3,723,064 A | 3/1973 | Liotta | |
| 3,741,197 A | 6/1973 | Sanz et al. | |
| 3,961,898 A | 6/1976 | Neeley et al. | |
| 3,992,158 A | 11/1976 | Przybylowicz et al. | |
| 4,014,328 A | 3/1977 | Cluff et al. | |
| 4,042,335 A | 8/1977 | Clement | |
| 4,057,394 A | 11/1977 | Genshaw | |
| 4,109,655 A | 8/1978 | Chacornac | |
| 4,250,257 A | 2/1981 | Lee et al. | |
| 4,253,083 A | 2/1981 | Imamura | |
| 4,254,083 A | 3/1981 | Columbus | |
| 4,258,001 A | 3/1981 | Pierce et al. | |
| 4,260,257 A | 4/1981 | Neeley et al. | |
| 4,289,459 A | 9/1981 | Neeley et al. | |
| 4,321,397 A | 3/1982 | Nix et al. | |
| 4,350,762 A | 9/1982 | DeLuca et al. | |
| 4,394,512 A | 7/1983 | Batz | |
| 4,414,975 A | 11/1983 | Ryder et al. | |
| 4,416,279 A | 11/1983 | Lindner et al. | |
| 4,418,037 A | 11/1983 | Katsuyama et al. | |
| 4,422,941 A | 12/1983 | Vaughan, Jr. et al. | |
| 4,429,700 A | 2/1984 | Thees et al. | |
| 4,627,445 A | 12/1986 | Garcia et al. | |
| 4,637,403 A | 1/1987 | Garcia et al. | |
| 4,637,406 A | 1/1987 | Guinn et al. | |
| 4,653,513 A | 3/1987 | Dombrowski | |
| 4,661,319 A | 4/1987 | Lape | |
| 4,702,261 A | 10/1987 | Cornell et al. | |
| 4,711,250 A | 12/1987 | Gilbaugh, Jr. et al. | |
| 4,737,458 A | 4/1988 | Batz et al. | |
| 4,767,415 A | 8/1988 | Duffy | |
| 4,774,192 A | 9/1988 | Terminiello et al. | |
| 4,787,398 A | 11/1988 | Garcia et al. | |
| 4,790,979 A | 12/1988 | Terminiello et al. | |
| 4,794,926 A | 1/1989 | Munsch et al. | |
| 4,815,843 A | 3/1989 | Tiefenthaler et al. | |
| 4,829,470 A | 5/1989 | Wang | |
| 4,844,095 A | 7/1989 | Chiodo et al. | |
| 4,846,785 A | 7/1989 | Cassou et al. | |
| 4,887,306 A | 12/1989 | Hwang et al. | |
| 4,920,977 A | 5/1990 | Haynes | |
| 4,929,426 A | 5/1990 | Bodai et al. | |
| 4,930,525 A | 6/1990 | Palestrant | |
| 4,935,346 A | 6/1990 | Phillips | |
| 4,953,552 A | 9/1990 | De Marzo | |
| 4,966,646 A | 10/1990 | Zdeblick | |
| 4,983,178 A | 1/1991 | Schnell | |
| 4,995,402 A | 2/1991 | Smith | |
| 5,029,583 A | 7/1991 | Meserol | |
| 5,035,704 A | 7/1991 | Lambert et al. | |
| 5,049,487 A | 9/1991 | Phillips et al. | |
| 5,050,617 A | 9/1991 | Columbus et al. | |
| 5,059,394 A | 10/1991 | Phillips et al. | |
| 5,077,199 A | 12/1991 | Basagni et al. | |
| 5,094,943 A | 3/1992 | Siedel et al. | |
| 5,110,724 A | 5/1992 | Hewett | |
| 5,114,350 A | 5/1992 | Hewett | |
| 5,116,759 A | 5/1992 | Klainer et al. | |
| 5,131,404 A | 7/1992 | Neeley et al. | |
| 5,141,868 A | 8/1992 | Shanks et al. | |
| 5,145,565 A | 9/1992 | Kater et al. | |
| 5,146,437 A | 9/1992 | Boucheron | |
| 5,153,416 A | 10/1992 | Neeley | |
| 5,164,575 A | 11/1992 | Neeley et al. | |
| 5,166,498 A | 11/1992 | Neeley | |
| 5,174,291 A | 12/1992 | Schoonen et al. | |
| 5,176,632 A | 1/1993 | Bernardi | |
| 5,179,005 A | 1/1993 | Phillips et al. | |
| 5,183,741 A | 2/1993 | Arai et al. | |
| 5,196,302 A | 3/1993 | Kidwell | |
| 5,208,163 A | 5/1993 | Charlton et al. | |
| 5,213,966 A | 5/1993 | Vuorinen et al. | |
| 5,217,480 A | 6/1993 | Habar et al. | |
| 5,218,966 A | 6/1993 | Yamasawa | |
| 5,223,219 A | 6/1993 | Subramanian et al. | |
| 5,228,972 A | 7/1993 | Osaka et al. | |
| 5,234,818 A | 8/1993 | Zimmermann et al. | |
| 5,241,969 A | 9/1993 | Carson et al. | |
| 5,251,126 A | 10/1993 | Kahn et al. | |
| D341,848 S | 11/1993 | Bigelow et al. | |
| 5,269,800 A | 12/1993 | Davis, Jr. | |
| 5,275,159 A | 1/1994 | Griebel | |
| 5,278,079 A | 1/1994 | Gubinski et al. | |
| 5,279,294 A | 1/1994 | Anderson et al. | |
| 5,288,646 A | 2/1994 | Lundsgaard et al. | |
| 5,299,571 A | 4/1994 | Mastrototaro | |
| 5,301,686 A | 4/1994 | Newman | |
| 5,302,513 A | 4/1994 | Mike et al. | |
| 5,304,468 A | 4/1994 | Phillips et al. | |
| 5,306,623 A | 4/1994 | Kiser et al. | |
| 5,308,767 A | 5/1994 | Terashima | |
| 5,314,441 A | 5/1994 | Cusack et al. | |
| 5,320,607 A | 6/1994 | Ishibashi | |
| 5,354,537 A | 10/1994 | Moreno | |
| 5,360,595 A | 11/1994 | Bell et al. | |
| 5,368,047 A | 11/1994 | Suzuki et al. | |
| 5,383,512 A | 1/1995 | Jarvis | |
| 5,390,671 A | 2/1995 | Lord et al. | |
| 5,395,388 A | 3/1995 | Schraga | |
| 5,399,316 A | 3/1995 | Yamada | |
| 5,401,110 A | 3/1995 | Neeley | |
| 5,402,798 A | 4/1995 | Swierczek et al. | |
| 5,426,032 A | 6/1995 | Phillips et al. | |
| 5,441,513 A | 8/1995 | Roth | |
| 5,451,350 A | 9/1995 | Macho et al. | |
| 5,458,140 A | 10/1995 | Eppstein et al. | |
| 5,460,777 A | 10/1995 | Kitajima et al. | |
| 5,460,968 A | 10/1995 | Yoshida et al. | |

(56) References Cited

U.S. PATENT DOCUMENTS

| | | |
|---|---|---|
| 5,482,473 A | 1/1996 | Lord et al. |
| 5,506,200 A | 4/1996 | Hirschkoff et al. |
| 5,507,288 A | 4/1996 | Böcker et al. |
| 5,508,200 A | 4/1996 | Tiffany et al. |
| 5,510,266 A | 4/1996 | Bonner et al. |
| 5,514,152 A | 5/1996 | Smith |
| 5,525,518 A | 6/1996 | Lundsgaard et al. |
| 5,527,892 A | 6/1996 | Borsotti et al. |
| 5,563,042 A | 10/1996 | Phillips et al. |
| 5,568,806 A | 10/1996 | Cheney, II et al. |
| 5,569,287 A | 10/1996 | Tezuka et al. |
| 5,575,403 A | 11/1996 | Charlton et al. |
| 5,577,499 A | 11/1996 | Teves |
| 5,582,184 A | 12/1996 | Erickson et al. |
| 5,586,553 A | 12/1996 | Halili et al. |
| 5,591,139 A | 1/1997 | Lin et al. |
| 5,593,838 A | 1/1997 | Zanzucchi et al. |
| 5,611,809 A | 3/1997 | Marshall et al. |
| 5,624,458 A | 4/1997 | Lipscher |
| 5,630,986 A | 5/1997 | Charlton et al. |
| 5,632,410 A | 5/1997 | Moulton et al. |
| 5,636,632 A | 6/1997 | Bommannan et al. |
| 5,647,851 A | 7/1997 | Pokras |
| 5,658,515 A | 8/1997 | Lee et al. |
| 5,660,791 A | 8/1997 | Brenneman et al. |
| 5,670,031 A | 9/1997 | Hintsche et al. |
| 5,676,850 A | 10/1997 | Reed et al. |
| 5,680,858 A | 10/1997 | Hansen et al. |
| 5,681,484 A | 10/1997 | Zanzucchi et al. |
| 5,682,233 A | 10/1997 | Brinda |
| 5,697,901 A | 12/1997 | Eriksson |
| 5,700,695 A | 12/1997 | Yassinzadeh et al. |
| 5,701,181 A | 12/1997 | Boiarski et al. |
| 5,701,910 A | 12/1997 | Powles et al. |
| D389,761 S | 1/1998 | Thomas |
| 5,705,018 A | 1/1998 | Hartley |
| 5,708,247 A | 1/1998 | McAleer |
| 5,708,787 A | 1/1998 | Nakano et al. |
| 5,715,417 A | 2/1998 | Gardien et al. |
| 5,730,753 A | 3/1998 | Morita |
| 5,735,273 A | 4/1998 | Kurnik et al. |
| 5,736,103 A | 4/1998 | Pugh |
| 5,741,211 A | 4/1998 | Renirie et al. |
| 5,746,217 A | 5/1998 | Erickson et al. |
| 5,746,720 A | 5/1998 | Stouder, Jr. |
| 5,757,666 A | 5/1998 | Schreiber et al. |
| 5,759,364 A | 6/1998 | Charlton et al. |
| 5,766,066 A | 6/1998 | Ranniger |
| 5,771,890 A | 6/1998 | Tamada |
| 5,797,693 A | 8/1998 | Jaeger |
| 5,800,420 A | 9/1998 | Gross et al. |
| 5,801,057 A | 9/1998 | Smart et al. |
| 5,807,375 A | 9/1998 | Gross et al. |
| 5,820,570 A | 10/1998 | Erickson et al. |
| 5,827,183 A | 10/1998 | Kurnik et al. |
| 5,840,020 A | 11/1998 | Heinonen et al. |
| 5,841,126 A | 11/1998 | Fossum et al. |
| 5,843,692 A | 12/1998 | Phillips et al. |
| 5,846,837 A | 12/1998 | Thym et al. |
| 5,851,215 A | 12/1998 | Mawhirt et al. |
| 5,854,074 A | 12/1998 | Charlton et al. |
| D403,975 S | 1/1999 | Douglas et al. |
| 5,855,801 A | 1/1999 | Lin et al. |
| 5,856,195 A | 1/1999 | Charlton et al. |
| 5,858,194 A | 1/1999 | Bell |
| 5,866,281 A | 2/1999 | Guckel et al. |
| 5,871,494 A | 2/1999 | Simons et al. |
| 5,879,310 A | 3/1999 | Sopp et al. |
| 5,879,326 A | 3/1999 | Godshall et al. |
| 5,879,367 A | 3/1999 | Latterell et al. |
| 5,885,839 A | 3/1999 | Lingane et al. |
| 5,891,053 A | 4/1999 | Sesekura |
| 5,893,870 A | 4/1999 | Talen et al. |
| D411,621 S | 6/1999 | Eisenbarth et al. |
| 5,911,711 A | 6/1999 | Pelkey |
| 5,911,737 A | 6/1999 | Lee et al. |
| 5,912,139 A | 6/1999 | Iwata et al. |
| 5,925,021 A | 7/1999 | Castellano et al. |
| 5,928,207 A | 7/1999 | Pisano et al. |
| 5,930,873 A | 8/1999 | Wyser |
| 5,938,679 A | 8/1999 | Freeman et al. |
| 5,945,678 A | 8/1999 | Yanagisawa |
| 5,951,492 A | 9/1999 | Douglas et al. |
| 5,951,493 A | 9/1999 | Douglas et al. |
| 5,951,521 A | 9/1999 | Mastrototaro et al. |
| 5,954,685 A | 9/1999 | Tierney |
| 5,962,215 A | 10/1999 | Douglas et al. |
| 5,968,760 A | 10/1999 | Phillips et al. |
| 5,968,765 A | 10/1999 | Grage et al. |
| 5,968,836 A | 10/1999 | Matzinger et al. |
| 5,971,941 A | 10/1999 | Simons et al. |
| 5,972,294 A | 10/1999 | Smith et al. |
| 5,986,754 A | 11/1999 | Harding |
| 5,989,409 A | 11/1999 | Kurnik et al. |
| 5,993,189 A | 11/1999 | Mueller et al. |
| D417,504 S | 12/1999 | Love et al. |
| 6,001,067 A | 12/1999 | Shults et al. |
| 6,005,545 A | 12/1999 | Nishida et al. |
| 6,010,463 A | 1/2000 | Lauks et al. |
| 6,010,519 A | 1/2000 | Mawhirt et al. |
| 6,014,135 A | 1/2000 | Fernandes |
| 6,014,577 A | 1/2000 | Henning et al. |
| 6,023,629 A | 2/2000 | Tamada |
| 6,027,459 A | 2/2000 | Shain et al. |
| 6,030,827 A | 2/2000 | Davis et al. |
| 6,032,059 A | 2/2000 | Henning et al. |
| 6,036,924 A | 3/2000 | Simons et al. |
| 6,041,253 A | 3/2000 | Kost et al. |
| 6,045,753 A | 4/2000 | Loewy et al. |
| 6,048,352 A | 4/2000 | Douglas et al. |
| 6,050,988 A | 4/2000 | Zuck |
| 6,056,701 A | 5/2000 | Duchon et al. |
| 6,056,734 A | 5/2000 | Jacobsen et al. |
| 6,058,321 A | 5/2000 | Swayze et al. |
| 6,059,815 A | 5/2000 | Lee et al. |
| 6,061,128 A | 5/2000 | Zweig et al. |
| 6,063,039 A | 5/2000 | Cunningham et al. |
| 6,071,251 A | 6/2000 | Cunningham et al. |
| 6,071,294 A | 6/2000 | Simons et al. |
| 6,077,660 A | 6/2000 | Wong et al. |
| 6,080,116 A | 6/2000 | Erickson et al. |
| 6,083,196 A | 7/2000 | Trautman et al. |
| 6,086,544 A | 7/2000 | Hibner et al. |
| 6,090,790 A | 7/2000 | Eriksson |
| 6,091,975 A | 7/2000 | Daddona et al. |
| 6,093,156 A | 7/2000 | Cunningham et al. |
| 6,097,831 A | 8/2000 | Wieck et al. |
| 6,099,484 A | 8/2000 | Douglas et al. |
| 6,100,107 A | 8/2000 | Lei et al. |
| 6,102,933 A | 8/2000 | Lee et al. |
| 6,103,033 A | 8/2000 | Say et al. |
| 6,103,197 A | 8/2000 | Werner |
| 6,106,751 A | 8/2000 | Talbot et al. |
| 6,118,126 A | 9/2000 | Zanzucchi |
| 6,120,676 A | 9/2000 | Heller et al. |
| 6,123,861 A | 9/2000 | Santini, Jr. et al. |
| 6,126,899 A | 10/2000 | Woudenberg et al. |
| 6,132,449 A | 10/2000 | Lum et al. |
| 6,139,562 A | 10/2000 | Mauze et al. |
| 6,142,939 A | 11/2000 | Eppstein et al. |
| 6,152,942 A | 11/2000 | Brenneman et al. |
| 6,162,639 A | 12/2000 | Douglas |
| 6,172,743 B1 | 1/2001 | Kley et al. |
| 6,175,752 B1 | 1/2001 | Say et al. |
| 6,176,865 B1 | 1/2001 | Mauze et al. |
| 6,183,434 B1 | 2/2001 | Eppstein et al. |
| 6,183,489 B1 | 2/2001 | Douglas et al. |
| 6,187,210 B1 | 2/2001 | Lebouiz et al. |
| 6,192,891 B1 | 2/2001 | Gravel et al. |
| 6,193,873 B1 | 2/2001 | Ohara et al. |
| 6,200,296 B1 | 3/2001 | Dibiasi et al. |
| 6,206,841 B1 | 3/2001 | Cunningham et al. |
| 6,214,626 B1 | 4/2001 | Meller et al. |
| 6,219,574 B1 | 4/2001 | Cormier et al. |

(56) References Cited

U.S. PATENT DOCUMENTS

| | | |
|---|---|---|
| 6,228,100 B1 | 5/2001 | Schraga |
| 6,230,051 B1 | 5/2001 | Cormier et al. |
| 6,231,531 B1 | 5/2001 | Lum et al. |
| 6,241,862 B1 | 6/2001 | McAleer et al. |
| 6,242,207 B1 | 6/2001 | Douglas et al. |
| 6,245,215 B1 | 6/2001 | Douglas et al. |
| 6,251,083 B1 | 6/2001 | Yum et al. |
| 6,251,260 B1 | 6/2001 | Heller et al. |
| 6,254,586 B1 | 7/2001 | Mann et al. |
| 6,255,061 B1 | 7/2001 | Mori et al. |
| 6,256,533 B1 | 7/2001 | Yuzhakov et al. |
| 6,268,162 B1 | 7/2001 | Phillips et al. |
| 6,271,045 B1 | 8/2001 | Douglas et al. |
| 6,272,364 B1 | 8/2001 | Kurnik |
| 6,283,926 B1 | 9/2001 | Cunningham et al. |
| 6,289,230 B1 | 9/2001 | Chaiken et al. |
| 6,298,254 B2 | 10/2001 | Tamada |
| 6,299,578 B1 | 10/2001 | Kurnik et al. |
| 6,299,757 B1 | 10/2001 | Feldman et al. |
| 6,306,104 B1 | 10/2001 | Cunningham et al. |
| 6,309,351 B1 | 10/2001 | Kurnik et al. |
| D450,711 S | 11/2001 | Istvan et al. |
| 6,312,612 B1 | 11/2001 | Sherman et al. |
| 6,312,812 B1 | 11/2001 | Sherman et al. |
| 6,312,888 B1 | 11/2001 | Wong et al. |
| 6,315,738 B1 | 11/2001 | Nishikawa et al. |
| 6,322,808 B1 | 11/2001 | Trautman et al. |
| 6,329,161 B1 | 12/2001 | Heller et al. |
| 6,331,266 B1 | 12/2001 | Powell et al. |
| 6,332,871 B1 | 12/2001 | Douglas et al. |
| 6,334,856 B1 | 1/2002 | Allen et al. |
| 6,350,273 B1 | 2/2002 | Minagawa et al. |
| 6,352,514 B1 | 3/2002 | Douglas et al. |
| 6,356,776 B1 | 3/2002 | Berner et al. |
| 6,358,265 B1 | 3/2002 | Thorne, Jr. et al. |
| 6,364,890 B1 | 4/2002 | Lum et al. |
| 6,375,626 B1 | 4/2002 | Allen et al. |
| 6,375,627 B1 | 4/2002 | Mauze et al. |
| 6,379,969 B1 | 4/2002 | Mauze et al. |
| 6,391,005 B1 | 5/2002 | Lum et al. |
| 6,391,645 B1 | 5/2002 | Huang et al. |
| 6,402,704 B1 | 6/2002 | McMorrow |
| 6,409,679 B2 | 6/2002 | Pyo |
| 6,428,664 B1 | 8/2002 | Bhullar et al. |
| 6,449,608 B1 | 9/2002 | Morita et al. |
| 6,455,324 B1 | 9/2002 | Douglas |
| 6,493,069 B1 | 12/2002 | Nagashimada |
| 6,500,134 B1 | 12/2002 | Cassone |
| 6,520,973 B1 | 2/2003 | McGarry |
| 6,530,892 B1 | 3/2003 | Kelly |
| 6,537,243 B1 | 3/2003 | Henning et al. |
| 6,540,675 B2 | 4/2003 | Aceti et al. |
| 6,544,475 B1 | 4/2003 | Douglas et al. |
| 6,549,796 B2 | 4/2003 | Sohrab |
| 6,555,061 B1 | 4/2003 | Leong et al. |
| 6,558,624 B1 | 5/2003 | Lemmon et al. |
| 6,579,690 B1 | 6/2003 | Bonnecaze et al. |
| 6,589,260 B1 | 7/2003 | Schmelzeisen-Redeker et al. |
| 6,591,125 B1 | 7/2003 | Buse et al. |
| 6,602,205 B1 | 8/2003 | Erickson et al. |
| 6,612,111 B1 | 9/2003 | Hodges et al. |
| 6,616,616 B2 | 9/2003 | Fritz et al. |
| 6,626,874 B1 | 9/2003 | Duchamp |
| 6,656,167 B2 | 12/2003 | Numao et al. |
| 6,679,852 B1 | 1/2004 | Schmelzeisen-Redeker et al. |
| 6,706,000 B2 | 3/2004 | Perez et al. |
| 6,706,049 B2 | 3/2004 | Moerman |
| 6,706,159 B2 | 3/2004 | Moerman et al. |
| 6,707,554 B1 | 3/2004 | Miltner et al. |
| 6,740,800 B1 | 5/2004 | Cunningham |
| 6,743,635 B2 | 6/2004 | Neel et al. |
| 6,748,275 B2 | 6/2004 | Lattner et al. |
| 6,753,187 B2 | 6/2004 | Cizdziel et al. |
| 6,766,817 B2 | 7/2004 | da Silva |
| 6,793,633 B2 | 9/2004 | Douglas et al. |
| 6,830,669 B2 | 12/2004 | Miyazaki et al. |
| 6,836,678 B2 | 12/2004 | Tu |
| 6,837,858 B2 | 1/2005 | Cunningham et al. |
| 6,847,451 B2 | 1/2005 | Pugh |
| 6,849,052 B2 | 2/2005 | Uchigaki et al. |
| 6,896,850 B2 | 5/2005 | Subramanian et al. |
| 6,918,404 B2 | 7/2005 | Da Silva |
| 6,919,960 B2 | 7/2005 | Hansen et al. |
| 6,923,764 B2 | 8/2005 | Aceti et al. |
| 6,936,476 B1 | 8/2005 | Anderson et al. |
| D511,214 S | 11/2005 | Sasano et al. |
| 6,988,996 B2 | 1/2006 | Roe et al. |
| 7,004,928 B2 | 2/2006 | Aceti et al. |
| 7,011,630 B2 | 3/2006 | Desai et al. |
| 7,025,774 B2 | 4/2006 | Freeman et al. |
| D519,868 S | 5/2006 | Sasano et al. |
| 7,052,652 B2 | 5/2006 | Zanzucchi et al. |
| 7,066,586 B2 | 6/2006 | Da Silva |
| 7,066,890 B1 | 6/2006 | Lam et al. |
| 7,141,058 B2 | 11/2006 | Briggs et al. |
| 7,156,809 B2 | 1/2007 | Quy |
| 7,163,616 B2 | 1/2007 | Vreeke et al. |
| 7,192,061 B2 | 3/2007 | Martin |
| D540,343 S | 4/2007 | Cummins |
| 7,223,365 B2 | 5/2007 | Von Der Goltz |
| 7,225,008 B1 | 5/2007 | Ward et al. |
| 7,226,461 B2 | 6/2007 | Boecker et al. |
| 7,258,673 B2 | 8/2007 | Racchini et al. |
| D551,243 S | 9/2007 | Young |
| 7,270,970 B2 | 9/2007 | Anderson et al. |
| 7,297,151 B2 | 11/2007 | Boecker et al. |
| 7,299,081 B2 | 11/2007 | Mace et al. |
| 7,343,188 B2 | 3/2008 | Sohrab |
| 7,344,507 B2 | 3/2008 | Briggs et al. |
| 7,379,167 B2 | 5/2008 | Mawhirt et al. |
| 7,427,377 B2 | 9/2008 | Zanzucchi et al. |
| D580,068 S | 11/2008 | Shigesada et al. |
| D580,558 S | 11/2008 | Shigesada et al. |
| D599,373 S | 9/2009 | Kobayashi et al. |
| D601,257 S | 9/2009 | Berlinger |
| 7,585,278 B2 | 9/2009 | Aceti et al. |
| D601,444 S | 10/2009 | Jones et al. |
| D601,578 S | 10/2009 | Poulet et al. |
| 7,682,318 B2 | 3/2010 | Alden et al. |
| D622,393 S | 8/2010 | Gatrall et al. |
| 7,780,631 B2 | 8/2010 | Lum et al. |
| 7,803,123 B2 | 9/2010 | Perez et al. |
| 7,850,621 B2 | 12/2010 | Briggs et al. |
| 7,879,058 B2 | 2/2011 | Ikeda |
| 7,887,494 B2 | 2/2011 | Emery et al. |
| D642,191 S | 7/2011 | Barnett et al. |
| 7,988,644 B2 | 8/2011 | Freeman et al. |
| 8,012,103 B2 | 9/2011 | Escutia et al. |
| 8,012,104 B2 | 9/2011 | Escutia et al. |
| 8,105,849 B2 | 1/2012 | McDevitt et al. |
| D654,926 S | 2/2012 | Lipman et al. |
| 8,173,439 B2 | 5/2012 | Petrich et al. |
| 8,184,273 B2 | 5/2012 | Dosmann et al. |
| 8,231,832 B2 | 7/2012 | Zanzucchi et al. |
| 8,251,920 B2 | 8/2012 | Vreeke et al. |
| 8,298,255 B2 | 10/2012 | Conway et al. |
| 8,303,518 B2 | 11/2012 | Aceti et al. |
| 8,360,993 B2 | 1/2013 | Escutia et al. |
| 8,360,994 B2 | 1/2013 | Escutia et al. |
| 8,372,015 B2 | 2/2013 | Escutia et al. |
| 8,376,959 B2 | 2/2013 | Deck |
| 8,382,681 B2 | 2/2013 | Escutia et al. |
| 8,391,940 B2 | 3/2013 | Matzinger et al. |
| D691,174 S | 10/2013 | Lipman et al. |
| 8,574,168 B2 | 11/2013 | Freeman et al. |
| 8,702,624 B2 | 4/2014 | Alden |
| 8,795,201 B2 | 8/2014 | Escutia et al. |
| 8,801,631 B2 | 8/2014 | Escutia et al. |
| 8,919,605 B2 | 12/2014 | Lipman et al. |
| 8,969,097 B2 | 3/2015 | Emery et al. |
| 9,060,723 B2 | 6/2015 | Escutia et al. |
| 9,060,727 B2 | 6/2015 | Saikley et al. |
| 9,095,292 B2 | 8/2015 | Zanzucchi et al. |
| 9,149,215 B2 | 10/2015 | Werner et al. |

(56) References Cited

U.S. PATENT DOCUMENTS

| | | |
|---|---|---|
| 9,366,636 B2 | 6/2016 | Emery et al. |
| 9,380,974 B2 | 7/2016 | Litherland et al. |
| 9,603,562 B2 | 3/2017 | Aceti et al. |
| 9,636,051 B2 | 5/2017 | Emery et al. |
| 9,782,114 B2 | 10/2017 | Reynolds et al. |
| 9,833,183 B2 | 12/2017 | Escutia et al. |
| 9,839,384 B2 | 12/2017 | Escutia et al. |
| 9,897,610 B2 | 2/2018 | Lipman et al. |
| 10,226,208 B2 | 3/2019 | Emery et al. |
| 10,330,667 B2 | 6/2019 | Lipman et al. |
| 10,383,556 B2 | 8/2019 | Lipman et al. |
| 10,433,780 B2 | 10/2019 | Escutia et al. |
| 10,441,205 B2 | 10/2019 | Litherland et al. |
| 2001/0001034 A1 | 5/2001 | Douglas |
| 2001/0027277 A1 | 10/2001 | Klitmose |
| 2001/0027328 A1 | 10/2001 | Lum et al. |
| 2001/0053891 A1 | 12/2001 | Ackley |
| 2002/0002326 A1 | 1/2002 | Causey, III et al. |
| 2002/0002344 A1 | 1/2002 | Douglas et al. |
| 2002/0004640 A1 | 1/2002 | Conn et al. |
| 2002/0006355 A1 | 1/2002 | Whitson |
| 2002/0016568 A1 | 2/2002 | Lebel et al. |
| 2002/0020688 A1 | 2/2002 | Sherman et al. |
| 2002/0022934 A1 | 2/2002 | Vogel et al. |
| 2002/0023852 A1 | 2/2002 | McIvor et al. |
| 2002/0042594 A1 | 4/2002 | Lum et al. |
| 2002/0045243 A1 | 4/2002 | Laska et al. |
| 2002/0052618 A1 | 5/2002 | Haar et al. |
| 2002/0087056 A1 | 7/2002 | Aceti et al. |
| 2002/0136667 A1 | 9/2002 | Subramanian et al. |
| 2002/0137998 A1 | 9/2002 | Smart et al. |
| 2002/0160520 A1 | 10/2002 | Orloff et al. |
| 2002/0168290 A1 | 11/2002 | Yuzhakov et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0177764 A1 | 11/2002 | Sohrab |
| 2002/0183102 A1 | 12/2002 | Withers et al. |
| 2002/0188223 A1 | 12/2002 | Perez et al. |
| 2002/0198444 A1 | 12/2002 | Uchigaki et al. |
| 2003/0012693 A1 | 1/2003 | Otillar et al. |
| 2003/0028087 A1 | 2/2003 | Yuzhakov et al. |
| 2003/0028125 A1 | 2/2003 | Yuzhakov et al. |
| 2003/0039587 A1 | 2/2003 | Niermann |
| 2003/0060730 A1 | 3/2003 | Perez |
| 2003/0083685 A1 | 5/2003 | Freeman et al. |
| 2003/0083686 A1 | 5/2003 | Freeman et al. |
| 2003/0105961 A1 | 6/2003 | Zatloukal et al. |
| 2003/0116596 A1 | 6/2003 | Terasawa |
| 2003/0135166 A1 | 7/2003 | Gonnelli |
| 2003/0135333 A1 | 7/2003 | Aceti |
| 2003/0143746 A1 | 7/2003 | Sage |
| 2003/0153844 A1 | 8/2003 | Smith et al. |
| 2003/0153900 A1 | 8/2003 | Aceti et al. |
| 2003/0175987 A1 | 9/2003 | Verdonk et al. |
| 2003/0206302 A1 | 11/2003 | Pugh |
| 2003/0207441 A1 | 11/2003 | Eyster et al. |
| 2003/0208113 A1 | 11/2003 | Mault et al. |
| 2003/0208140 A1 | 11/2003 | Pugh |
| 2003/0211617 A1 | 11/2003 | Jones |
| 2003/0211619 A1 | 11/2003 | Olson et al. |
| 2003/0212344 A1 | 11/2003 | Yuzhakov et al. |
| 2003/0212345 A1 | 11/2003 | McAllister et al. |
| 2003/0212347 A1 | 11/2003 | Sohrab |
| 2003/0216628 A1 | 11/2003 | Bortz et al. |
| 2004/0010207 A1 | 1/2004 | Flaherty et al. |
| 2004/0030353 A1 | 2/2004 | Schmelzeisen-redeker et al. |
| 2004/0039303 A1 | 2/2004 | Wurster et al. |
| 2004/0049219 A1 | 3/2004 | Briggs et al. |
| 2004/0059256 A1 | 3/2004 | Perez |
| 2004/0072357 A1 | 4/2004 | Stiene et al. |
| 2004/0073140 A1 | 4/2004 | Douglas |
| 2004/0092842 A1 | 5/2004 | Boecker et al. |
| 2004/0092995 A1 | 5/2004 | Boecker et al. |
| 2004/0094432 A1 | 5/2004 | Neel et al. |
| 2004/0096959 A1 | 5/2004 | Stiene et al. |
| 2004/0097796 A1 | 5/2004 | Berman et al. |
| 2004/0098009 A1 | 5/2004 | Boecker et al. |
| 2004/0102803 A1 | 5/2004 | Boecker et al. |
| 2004/0122339 A1 | 6/2004 | Roe et al. |
| 2004/0132167 A1 | 7/2004 | Rule et al. |
| 2004/0138588 A1 | 7/2004 | Saikley et al. |
| 2004/0155084 A1 | 8/2004 | Brown |
| 2004/0157339 A1 | 8/2004 | Burke et al. |
| 2004/0178218 A1 | 9/2004 | Schomakers et al. |
| 2004/0186394 A1 | 9/2004 | Roe et al. |
| 2004/0191119 A1 | 9/2004 | Zanzucchi et al. |
| 2004/0202576 A1 | 10/2004 | Aceti et al. |
| 2004/0230216 A1 | 11/2004 | LeVaughn et al. |
| 2004/0236251 A1 | 11/2004 | Roe et al. |
| 2004/0238675 A1 | 12/2004 | Banaszkiewicz et al. |
| 2004/0242982 A1 | 12/2004 | Sakata et al. |
| 2004/0249253 A1 | 12/2004 | Racchini et al. |
| 2004/0259180 A1 | 12/2004 | Burke et al. |
| 2005/0004494 A1 | 1/2005 | Perez et al. |
| 2005/0010134 A1 | 1/2005 | Douglas et al. |
| 2005/0015020 A1 | 1/2005 | LeVaughn et al. |
| 2005/0027182 A1 | 2/2005 | Siddiqui et al. |
| 2005/0038680 A1 | 2/2005 | McMahon |
| 2005/0070819 A1 | 3/2005 | Poux et al. |
| 2005/0096686 A1 | 5/2005 | Allen |
| 2005/0106713 A1 | 5/2005 | Phan et al. |
| 2005/0109386 A1 | 5/2005 | Marshall |
| 2005/0159678 A1 | 7/2005 | Taniike et al. |
| 2005/0187532 A1 | 8/2005 | Thurau et al. |
| 2005/0192492 A1 | 9/2005 | Cho et al. |
| 2005/0202567 A1 | 9/2005 | Zanzucchi et al. |
| 2005/0202733 A1 | 9/2005 | Yoshimura et al. |
| 2005/0209518 A1 | 9/2005 | Sage, Jr. et al. |
| 2005/0215872 A1 | 9/2005 | Berner et al. |
| 2005/0215923 A1 | 9/2005 | Wiegel |
| 2005/0245844 A1 | 11/2005 | Mace et al. |
| 2005/0255001 A1 | 11/2005 | Padmaabhan et al. |
| 2005/0277972 A1 | 12/2005 | Wong et al. |
| 2006/0008389 A1 | 1/2006 | Sacherer et al. |
| 2006/0036134 A1 | 2/2006 | Tarassenko et al. |
| 2006/0052724 A1 | 3/2006 | Roe |
| 2006/0064035 A1 | 3/2006 | Wang et al. |
| 2006/0079809 A1 | 4/2006 | Goldberger et al. |
| 2006/0094985 A1 | 5/2006 | Aceti et al. |
| 2006/0117616 A1 | 6/2006 | Jones et al. |
| 2006/0122536 A1 | 6/2006 | Haar et al. |
| 2006/0135873 A1 | 6/2006 | Karo et al. |
| 2006/0155317 A1 | 7/2006 | List |
| 2006/0161078 A1 | 7/2006 | Schraga |
| 2006/0178600 A1 | 8/2006 | Kennedy et al. |
| 2006/0189908 A1 | 8/2006 | Kennedy |
| 2006/0204399 A1 | 9/2006 | Freeman et al. |
| 2006/0229533 A1 | 10/2006 | Hoenes et al. |
| 2006/0241517 A1 | 10/2006 | Fowler et al. |
| 2006/0257993 A1 | 11/2006 | Mcdevitt et al. |
| 2006/0259102 A1 | 11/2006 | Slatkine |
| 2006/0281187 A1 | 12/2006 | Emery et al. |
| 2007/0016104 A1 | 1/2007 | Jansen et al. |
| 2007/0017824 A1 | 1/2007 | Rippeth et al. |
| 2007/0033074 A1 | 2/2007 | Nitzan et al. |
| 2007/0060842 A1 | 3/2007 | Alvarez-Icaza et al. |
| 2007/0078313 A1 | 4/2007 | Emery et al. |
| 2007/0078358 A1 | 4/2007 | Escutia et al. |
| 2007/0083130 A1 | 4/2007 | Thomson et al. |
| 2007/0083131 A1 | 4/2007 | Escutia et al. |
| 2007/0093786 A1 | 4/2007 | Goldsmith et al. |
| 2007/0112281 A1 | 5/2007 | Olson |
| 2007/0179404 A1 | 8/2007 | Escutia et al. |
| 2007/0179405 A1 | 8/2007 | Emery et al. |
| 2007/0253531 A1 | 11/2007 | Okuzawa et al. |
| 2007/0255181 A1 | 11/2007 | Alvarez-icaza et al. |
| 2007/0255302 A1 | 11/2007 | Koeppel et al. |
| 2008/0004601 A1 | 1/2008 | Jennewine et al. |
| 2008/0012701 A1 | 1/2008 | Kass et al. |
| 2008/0046831 A1 | 2/2008 | Imai et al. |
| 2008/0064986 A1 | 3/2008 | Kraemer et al. |
| 2008/0077048 A1 | 3/2008 | Escutia et al. |
| 2008/0119702 A1 | 5/2008 | Reggiardo |

(56) References Cited

U.S. PATENT DOCUMENTS

| | | | |
|---|---|---|---|
| 2008/0139910 A1 | 6/2008 | Mastrototaro et al. | |
| 2008/0194934 A1 | 8/2008 | Ray et al. | |
| 2008/0268485 A1 | 10/2008 | Guarino et al. | |
| 2008/0269625 A1 | 10/2008 | Halperin et al. | |
| 2009/0054810 A1 | 2/2009 | Zanzucchi et al. | |
| 2009/0149717 A1 | 6/2009 | Brauer et al. | |
| 2009/0149729 A1 | 6/2009 | Young et al. | |
| 2009/0156923 A1 | 6/2009 | Power et al. | |
| 2009/0292489 A1 | 11/2009 | Burke et al. | |
| 2009/0301899 A1 | 12/2009 | Hodges et al. | |
| 2010/0010374 A1 | 1/2010 | Escutia et al. | |
| 2010/0021947 A1 | 1/2010 | Emery et al. | |
| 2010/0021948 A1 | 1/2010 | Lipman et al. | |
| 2010/0095229 A1 | 4/2010 | Dixon et al. | |
| 2010/0174211 A1 | 7/2010 | Frey et al. | |
| 2010/0185120 A1 | 7/2010 | Sacherer et al. | |
| 2010/0217155 A1 | 8/2010 | Poux et al. | |
| 2010/0331650 A1 | 12/2010 | Batman et al. | |
| 2011/0098599 A1 | 4/2011 | Emery et al. | |
| 2011/0105872 A1 | 5/2011 | Chickering et al. | |
| 2011/0201909 A1 | 8/2011 | Emery et al. | |
| 2012/0166090 A1 | 6/2012 | Lipman et al. | |
| 2012/0271197 A1* | 10/2012 | Castle | A61B 5/150022 600/583 |
| 2012/0296179 A1 | 11/2012 | Zanzucchi et al. | |
| 2013/0110516 A1 | 5/2013 | Abulhaj et al. | |
| 2013/0158430 A1 | 6/2013 | Aceti et al. | |
| 2013/0158432 A1 | 6/2013 | Escutia et al. | |
| 2013/0172698 A1 | 7/2013 | Reynolds et al. | |
| 2013/0274568 A1 | 10/2013 | Escutia et al. | |
| 2013/0274579 A1 | 10/2013 | Richter et al. | |
| 2014/0012116 A1 | 1/2014 | Okuyama | |
| 2014/0316301 A1 | 10/2014 | Escutia et al. | |
| 2014/0336480 A1 | 11/2014 | Escutia et al. | |
| 2015/0037898 A1 | 2/2015 | Baldus et al. | |
| 2015/0153351 A1 | 6/2015 | Lipman et al. | |
| 2015/0212006 A1 | 7/2015 | Emery et al. | |
| 2015/0238131 A1* | 8/2015 | Richter | A61B 5/150022 600/583 |
| 2016/0038066 A1 | 2/2016 | Escutia et al. | |
| 2016/0367178 A1 | 12/2016 | Emery et al. | |
| 2017/0095188 A1 | 4/2017 | Emery et al. | |
| 2017/0319121 A1 | 11/2017 | Aceti et al. | |
| 2017/0354355 A1 | 12/2017 | Emery et al. | |
| 2018/0008178 A1 | 1/2018 | Reynolds et al. | |
| 2018/0214059 A1 | 8/2018 | Escutia et al. | |
| 2018/0296143 A1 | 10/2018 | Anderson et al. | |
| 2018/0310865 A1 | 11/2018 | Escutia et al. | |
| 2019/0025318 A1 | 1/2019 | Lipman et al. | |
| 2019/0104976 A1 | 4/2019 | Reynolds et al. | |
| 2019/0209064 A1 | 7/2019 | Emery et al. | |
| 2019/0391129 A1 | 12/2019 | Lipman et al. | |

FOREIGN PATENT DOCUMENTS

| | | |
|---|---|---|
| DE | 197 05 091 A1 | 2/1999 |
| DE | 199 22 413 A1 | 11/2000 |
| DE | 103 02-501 A1 | 8/2004 |
| EP | 0 103 426 A2 | 3/1984 |
| EP | 0 256 806 A2 | 2/1988 |
| EP | 0 396-016 A2 | 11/1990 |
| EP | 0 396-016 A3 | 11/1990 |
| EP | 0 397 424 A2 | 11/1990 |
| EP | 0 762 311 A2 | 3/1997 |
| EP | 0 255-338 A2 | 2/1998 |
| EP | 0 849 584 A2 | 6/1998 |
| EP | 1 266-607 A2 | 12/2002 |
| EP | 1 266-607 A3 | 12/2002 |
| EP | 1 369 688 A2 | 10/2003 |
| EP | 1 369 688 A3 | 10/2003 |
| EP | 1 360-934 A1 | 11/2003 |
| EP | 1 360-934 B1 | 11/2003 |
| EP | 1 486-766 A1 | 12/2004 |
| EP | 1 486-766 B1 | 12/2004 |
| EP | 1 529-489 A1 | 5/2005 |
| EP | 1 529-489 B1 | 5/2005 |
| EP | 1 769-735 A1 | 4/2007 |
| EP | 1 987 766 A2 | 11/2008 |
| JP | 63-305841 A | 12/1988 |
| JP | 3-63570 A | 3/1991 |
| JP | 03093189 A | 4/1991 |
| JP | 7-67861 A | 3/1995 |
| JP | 7-213925 A | 8/1995 |
| JP | 9-168530 A | 6/1997 |
| JP | 9-313465 A | 9/1997 |
| JP | 9-266889 A | 10/1997 |
| JP | 9-294737 A | 11/1997 |
| JP | 10-024028 A | 1/1998 |
| JP | 10-505258 A | 5/1998 |
| JP | 10-508518 A | 8/1998 |
| JP | 10-318970 A | 12/1998 |
| JP | 11056822 A | 3/1999 |
| JP | 11281779 A | 10/1999 |
| JP | 2000-116629 A | 4/2000 |
| JP | 2000-126161 A | 5/2000 |
| JP | 2000-168754 A | 6/2000 |
| JP | 2000-254111 A | 9/2000 |
| JP | 2001-159618 A | 6/2001 |
| JP | 2001-515203 A | 9/2001 |
| JP | 2001-305096 A | 10/2001 |
| JP | 2001-330581 A | 11/2001 |
| JP | 2002-502045 A | 1/2002 |
| JP | 2002-085384 A | 3/2002 |
| JP | 2002-514453 A | 5/2002 |
| JP | 2002-168862 A | 6/2002 |
| JP | 2003-507719 A | 2/2003 |
| JP | 2003-108679 A | 4/2003 |
| JP | 2003-180417 A2 | 7/2003 |
| JP | 2004-000598 A | 1/2004 |
| JP | 2004-500948 A | 1/2004 |
| JP | 2004-117339 A | 4/2004 |
| JP | 2004-202256 A | 7/2004 |
| JP | 2004-209266 A | 7/2004 |
| JP | 2004-519302 A | 7/2004 |
| JP | 2004-522500 A | 7/2004 |
| JP | 2004-528936 A | 9/2004 |
| JP | 2005-503538 A | 2/2005 |
| JP | 2005-087613 A | 4/2005 |
| JP | 2006-512969 A | 4/2005 |
| JP | 3638958 B2 | 4/2005 |
| JP | 2005-525149 A | 8/2005 |
| JP | 2005-237938 A | 9/2005 |
| JP | 2005-525846 A | 9/2005 |
| JP | 2005-527254 A | 9/2005 |
| JP | 2006-506185 A | 2/2006 |
| JP | 2006-512974 A | 4/2006 |
| JP | 2006-516723 A | 7/2006 |
| JP | 2006-521555 A | 9/2006 |
| JP | 2006-284481 A | 10/2006 |
| JP | 2006-527013 A | 11/2006 |
| JP | 2007-054407 A | 3/2007 |
| JP | 2007-067698 A | 3/2007 |
| JP | 2007-521031 A | 8/2007 |
| JP | 2007-527287 A | 9/2007 |
| JP | 2007-311196 A | 11/2007 |
| JP | 2007-537804 A | 12/2007 |
| JP | 2008-125813 A | 6/2008 |
| JP | 2008-212324 A | 9/2008 |
| JP | 2009-509645 A | 3/2009 |
| JP | 2009-509667 A | 3/2009 |
| JP | 2010-094167 A | 4/2010 |
| JP | 2012-213477 A | 11/2012 |
| WO | WO-86/05966 A1 | 10/1986 |
| WO | WO-88/00812 A1 | 2/1988 |
| WO | WO-88/07666 A1 | 10/1988 |
| WO | WO-91/14212 A1 | 9/1991 |
| WO | WO-94/13203 A1 | 6/1994 |
| WO | WO-95/10223 A2 | 4/1995 |
| WO | WO-95/10223 A3 | 4/1995 |
| WO | WO-96/04857 A1 | 2/1996 |
| WO | WO-96/07907 A1 | 3/1996 |
| WO | WO-96/14026 A1 | 5/1996 |
| WO | WO-96/25088 A1 | 8/1996 |

(56) References Cited

FOREIGN PATENT DOCUMENTS

| | | |
|---|---|---|
| WO | WO-97/15227 A1 | 5/1997 |
| WO | WO-97/29847 A1 | 8/1997 |
| WO | WO-97/30344 A1 | 8/1997 |
| WO | WO-97/41421 A1 | 11/1997 |
| WO | WO-97/42885 A1 | 11/1997 |
| WO | WO-97/42888 A1 | 11/1997 |
| WO | WO-97/43962 A1 | 11/1997 |
| WO | WO-98/00193 A1 | 1/1998 |
| WO | WO-98/31275 A1 | 7/1998 |
| WO | WO-98/35225 A1 | 8/1998 |
| WO | WO-99/12008 A1 | 3/1999 |
| WO | WO-99/23492 A1 | 5/1999 |
| WO | WO-99/44508 A1 | 9/1999 |
| WO | WO-99/56954 A1 | 11/1999 |
| WO | WO-99/58051 A1 | 11/1999 |
| WO | WO-99/62576 A1 | 12/1999 |
| WO | WO-00/09184 A1 | 2/2000 |
| WO | WO-00/13573 A1 | 3/2000 |
| WO | WO-00/14269 A1 | 3/2000 |
| WO | WO-00/14535 A1 | 3/2000 |
| WO | WO-00/18449 A2 | 4/2000 |
| WO | WO-00/18449 A3 | 4/2000 |
| WO | WO-00/19185 | 4/2000 |
| WO | WO-00/36400 A1 | 6/2000 |
| WO | WO-00/42422 A1 | 7/2000 |
| WO | WO-00/74763 A2 | 12/2000 |
| WO | WO-00/74763 A3 | 12/2000 |
| WO | WO-00/78208 A1 | 12/2000 |
| WO | WO-01/13795 A1 | 3/2001 |
| WO | WO-01/16575 A1 | 3/2001 |
| WO | WO-01/52727 A1 | 7/2001 |
| WO | WO-01/64105 A1 | 9/2001 |
| WO | WO-01/64105 C2 | 9/2001 |
| WO | WO-01/72220 A1 | 10/2001 |
| WO | WO-01/80728 A1 | 11/2001 |
| WO | WO-01/85233 A2 | 11/2001 |
| WO | WO-01/85233 A3 | 11/2001 |
| WO | WO-01/91634 A2 | 12/2001 |
| WO | WO-01/91634 A3 | 12/2001 |
| WO | WO-02/00101 A2 | 1/2002 |
| WO | WO-02/00101 A3 | 1/2002 |
| WO | WO-02/49507 A1 | 6/2002 |
| WO | WO-02/49509 A2 | 6/2002 |
| WO | WO-02/49509 A3 | 6/2002 |
| WO | WO-02/078533 A2 | 10/2002 |
| WO | WO-02/078533 A3 | 10/2002 |
| WO | WO-02/082052 A2 | 10/2002 |
| WO | WO-02/082052 A3 | 10/2002 |
| WO | WO-02/093144 A1 | 11/2002 |
| WO | WO-02/100251 A2 | 12/2002 |
| WO | WO-02/100251 A3 | 12/2002 |
| WO | WO-02/101359 A2 | 12/2002 |
| WO | WO-02/101359 A3 | 12/2002 |
| WO | WO-03/007819 A1 | 1/2003 |
| WO | WO-2003/030984 A1 | 4/2003 |
| WO | WO-2003/066128 A2 | 8/2003 |
| WO | WO-2003/066128 A3 | 8/2003 |
| WO | WO-2003/070099 A1 | 8/2003 |
| WO | WO-2003/071940 A1 | 9/2003 |
| WO | WO-2003/071940 C1 | 9/2003 |
| WO | WO-2004/045375 A2 | 6/2004 |
| WO | WO-2004/045375 A3 | 6/2004 |
| WO | WO-2004/062499 A1 | 7/2004 |
| WO | WO-2004/062500 A1 | 7/2004 |
| WO | WO-2004/062500 C1 | 7/2004 |
| WO | WO-2004/064636 A1 | 8/2004 |
| WO | WO-2004/085995 A2 | 10/2004 |
| WO | WO-2004/085995 A3 | 10/2004 |
| WO | WO-2004/091693 A2 | 10/2004 |
| WO | WO-2004/091693 A3 | 10/2004 |
| WO | WO-2004/105827 A2 | 12/2004 |
| WO | WO-2004/105827 A3 | 12/2004 |
| WO | WO-2005/006939 A2 | 1/2005 |
| WO | WO-2005/006939 A3 | 1/2005 |
| WO | WO-2005/009238 A1 | 2/2005 |
| WO | WO-2005/013824 A1 | 2/2005 |
| WO | WO-2005/018709 A2 | 3/2005 |
| WO | WO-2005/018709 A3 | 3/2005 |
| WO | WO-2005/018710 A2 | 3/2005 |
| WO | WO-2005/018710 A3 | 3/2005 |
| WO | WO-2005/084543 A1 | 9/2005 |
| WO | WO-2005/084546 A2 | 9/2005 |
| WO | WO-2005/084546 A3 | 9/2005 |
| WO | WO-2005/085995 A1 | 9/2005 |
| WO | WO-2005/112763 A1 | 12/2005 |
| WO | WO-2006/138226 A2 | 12/2006 |
| WO | WO-2006/138226 A3 | 12/2006 |
| WO | WO-2007/041062 A2 | 4/2007 |
| WO | WO-2007/041062 A3 | 4/2007 |
| WO | WO-2007/041063 A2 | 4/2007 |
| WO | WO-2007/041063 A3 | 4/2007 |
| WO | WO-2007/041244 A2 | 4/2007 |
| WO | WO-2007/041244 A3 | 4/2007 |
| WO | WO-2007/041287 A2 | 4/2007 |
| WO | WO-2007/041287 A3 | 4/2007 |
| WO | WO-2007/041355 A2 | 4/2007 |
| WO | WO-2007/041355 A3 | 4/2007 |
| WO | WO-2007/108519 A1 | 9/2007 |
| WO | WO-2007/112034 A2 | 10/2007 |
| WO | WO-2007/112034 A3 | 10/2007 |
| WO | WO-2007/131036 A1 | 11/2007 |
| WO | WO-2008/027319 A2 | 3/2008 |
| WO | WO-2008/027319 A3 | 3/2008 |
| WO | WO-2008/062648 A1 | 5/2008 |
| WO | WO-2009/145920 A1 | 12/2009 |
| WO | WO-2009/148624 A1 | 12/2009 |
| WO | WO-2009/148626 A1 | 12/2009 |
| WO | WO-2011/065981 A1 | 6/2011 |
| WO | WO-2011/162823 A1 | 12/2011 |
| WO | WO-2012/127870 A1 | 9/2012 |
| WO | WO-2013/020103 A1 | 2/2013 |
| WO | WO-2014/205412 A1 | 12/2014 |
| WO | WO-2018/191700 A1 | 10/2018 |

OTHER PUBLICATIONS

ADA (Jan. 1994). "Self-Monitoring of Blood Glucose," Consensus Statement *Diabetes Care* 17(1):81-86.

Anonymous. (Sep. 30, 1993). "The Effect of Intensive Treatment of Diabetes on the Development and Progression of Long-Term Complications in Insulin-Dependent Diabetes Mellitus." *The New England Journal of Medicine* 329(14):977-986.

Anonymous. (Jun. 23, 1998). Taking the "Ouch" Out of Needles: Arrays of "Microneedles" Offer New Techniques for Drug Delivery, *Science Daily*, located at <http:www.sciencedaily.com/releases/1998/06/980623045850.htm>, last visited Jan. 14, 2014, 3 pages.

Beregszàszi, M. et al. (Jul. 1997). "Nocturnal Hypoglycemia in Children and Adolescents with Insulin-Dependent Diabetes Mellitus: Prevalence and Risk Factors," *J. Pediatrics* 131(1 Pt. 1):27-33.

Chase, H.P. et al. (Feb. 2001). "Continuous Subcutaneous Glucose Monitoring in Children with Type 1 Diabetes," *Pediatrics* 107(2):222-226.

Clarke, W.L. et al. (Sep.-Oct. 1987). "Evaluating Clinical Accuracy of Systems for Self-Monitoring of Blood Glucose," *Diabetes Care* 10(5):622-628.

Collison, M.E. et al. (Sep. 1999). "Analytical Characterization of Electrochemical Biosensor Test Strips for Measurement of Glucose in Low-vol. Interstitial Fluid Samples," *Clinical Chemistry* 45(9):1665-1673.

Coster, S. et al. (2000). "Monitoring Blood Glucose Control in Diabetes Mellitus: A Systematic Review." *Health Technology Assessment* 4(12):1-93.

Cox, D.J. et al. (Jun. 1997). "Understanding Error Grid Analysis," *Diabetes Care* 20(6):911-912.

D'Arrigo, T.D. (Mar. 2000). "GlucoWatch Monitor Poised for Approval," *Diabetes Forecast*, 53(3):43-44.

Feldman, B. et al. (2000). "FreeStyle™: A Small-Volume Electrochemical Glucose Sensor for Home Blood Glucose Testing," *Diabetes Technology and Therapeutics*, 2(2):221-229.

(56) References Cited

OTHER PUBLICATIONS

Johnson, R.N. et al. (Jan. 1998). "Accuracy of Devices Used for Self-Monitoring of Blood Glucose," *Annals of Clinical Biochemistry* 35(1):68-74.
Johnson, R.N. et al. (Jan. 1999). "Analytical Error of Home Glucose Monitors: A Comparison of 18 Systems," *Annals of Clinical Biochemistry* 36(1):72-79.
Johnson, R.N. et al. (2001). "Error Detection and Measurement in Glucose Monitors," *Clinica Chimica Acta* 307:61-67.
Kumetrix, Inc. (Dec. 1999). "Painless Blood Glucose Monitoring, Courtesy of the Mosquito," *Start-Up* pp. 27-28.
Lee, S-C. (Jun. 1999). "Light Scattering by Closely Spaced Parallel Cylinders Embedded in a Finite Dielectric Slab," *Journal of the Optical Society of America A* 16(6):1350-1361.
McGarraugh, G. et al. (2001). "Physiological Influences on Off-Finger Glucose Testing," *Diabetes Technology & Therapeutics* 3(3):367-376.
McNichols, R.J. et al. (Jan. 2000). "Optical Glucose Sensing in Biological Fluids: An Overview," *Journal of Biomedical Optics*, 5(1):5-16.
Mahler, R.J. et al. (1999). "Clinical Review 102, Type 2 Diabetes Melitus: Update on Diagnosis Pathophysiology, and Treatment," *The Journal of Clinical Endocrinology and Metabolism* 84(4):1165-1171.
Medline Plus. (Jun. 17, 2008). , Medical Encyclopedia, Monitor Blood Glucose-Series: Part 1-4, 6 pages.
Neeley, W.E. et al. (1981). "An Instrument for Digital Matrix Photometry," *Clinical Chemistry* 27(10):1665-1668.
Neeley, W.E. (1983). "Reflectance Digital Matrix Photometry," *Clinical Chemistry* 29(6):1038-1041.
Neeley, W.E. (1983). "Multilayer Film Analysis for Glucose in 1-μL Samples of Plasma," *Clinical Chemistry* 29(12):2103-2105.
Neeley, W.E. (1988). "A Reflectance Photometer with a Square Photodiode Array Detector for Use on Multilayer Dry-Film Slides," *Clinical Chemistry* 34(11):2367-2370.
Otto, E. et al. (2000). "An Intelligent Diabetes Software Prototype: Predicting Blood Glucose Levels and Recommending Regimen Changes," *Diabetes Technology and Therapeutics* 2(4):569-576.
Pfohl, M. et al. (2000). "Spot Glucose Measurement in Epidermal Interstitial Fluid—An Alternative to Capillary Blood Glucose Estimation," *Experimental and Clinical Endocrinology & Diabetes* 108(1):1-4.
Princen, H.M. (May 1969). "Capillary Phenomena in Assemblies of Parallel Cylinders, I. Capillary Rise Between Two Cylinders," *Journal of Colloid and Interface Science* 30(1):69-75.
Princen, H.M. (Jul. 1969). "Capillary Phenomena in Assemblies of Parallel Cylinders, II. Capillary Rise in Systems with More Than Two Cylinders," *Journal of Colloid and Interface Science* 30(3):359-371.
Rebrin, K. et al. (Sep. 1999). "Subcutaneous Glucose Predicts Plasma Glucose Independent of Insulin: Implications for Continuous Monitoring," *American Journal of Physiology* 277(3):E561-E571.
Rosen, S. (1999). "Road to New-Age Glucose Monitoring Still Rocky," *Diagnostic Insight*, pp. 4-5, 12-13, 16.
Smart, W.H. et al. (2000). "The Use of Silicon Microfabrication Technology in Painless Glucose Monitoring, "*Diabetes Technology & Therapeutics* 2(4):549-559.
Svedman, C. et al. (Apr. 1999). "Skin Mini-Erosion Technique for Monitoring Metabolites in Interstitial Fluid: Its Feasibility Demonstrated by OGTT Results in Diabetic and Non-Diabetic Subjects," *Scand. J. Clin. Lab. Invest.* 59(2):115-123.
Trinder, P. (1969). "Determination of Glucose in Blood Using Glucose Oxidase with an Alternate Oxygen Acceptor," *Annals of Clinical Biochemistry* 6:24-28.
Yum, S. I. et al. (Nov. 1, 1999). "Capillary Blood Sampling for Self-Monitoring of Blood Glucose," *Diabetes Technology & Therapeutics*, 1(1):29-37.
Extended European Search Report dated Jun. 16, 2014, for EP Application No. 09758787.7, filed on Jun. 8, 2009, 6 pages.

Final Office Action dated May 8, 2012, for U.S. Appl. No. 12/457,331, filed Jun. 8, 2009, 7 pages.
Final Office Action dated Apr. 30, 2013, for U.S. Appl. No. 13/168,644, filed Jun. 24, 2011, 10 pages.
Final Office Action dated Mar. 27, 2014, for U.S. Appl. No. 12/457,332, filed Jun. 8, 2009, 10 pages.
Final Office Action dated Dec. 26, 2014, for U.S. Appl. No. 12/457,331, filed Jun. 8, 2009, 9 pages.
International Search Report dated Jul. 28, 2009, for PCT Application No. PCT/US2009/003441, filed on Jun. 8, 2009, 2 pages.
International Search Report dated Jul. 28, 2009, for PCT Application No. PCT/US2009/003445, filed on Jun. 8, 2009, 2 pages.
International Search Report dated Nov. 14, 2011, for PCT Application No. PCT/US2011/001132, filed on Jun. 24, 2011, 2 pages.
International Search Report dated Oct. 15, 2014 for PCT Application No. PCT/US2014/043516, filed on Jun. 20, 2014, 2 pages.
Non-Final Office Action dated Nov. 23, 2011, for U.S. Appl. No. 12/457,331, filed Jun. 8, 2009, 6 pages.
Non-Final Office Action dated Mar. 2, 2012, for U.S. Appl. No. 12/457,332, filed Jun. 8, 2009, 7 pages.
Non-Final Office Action dated Jun. 22, 2012, for U.S. Appl. No. 13/168,644, filed Jun. 24, 2011, 8 pages.
Non-Final Office Action dated May 30, 2013, for U.S. Appl. No. 12/457,332, filed Jun. 8, 2009, 9 pages.
Non-Final Office Action dated Jun. 13, 2014, for U.S. Appl. No. 12/457,331, filed Jun. 8, 2009, 8 pages.
Non-Final Office Action dated Jan. 13, 2015, for U.S. Appl. No. 13/168,644, filed Jun. 24, 2011, 12 pages.
Restriction Requirement dated Jul. 19, 2011, for U.S. Appl. No. 12/457,331, filed Jun. 8, 2009, 6 pages.
Written Opinion dated Jul. 28, 2009, for PCT Application No. PCT/US2009/003441, filed on Jun. 8, 2009, 10 pages.
Written Opinion dated Jul. 28, 2009, for PCT Application No. PCT/US2009/003445, filed on Jun. 8, 2009, 4 pages.
Written Opinion dated Nov. 14, 2011, for PCT Application No. PCT/US2011/001132, filed on Jun. 24, 2011, 6 pages.
Written Opinion dated Oct. 15, 2014 for PCT Application No. PCT/US2014/043516, filed on Jun. 20, 2014, 5 pages.
Final Office Action dated Sep. 30, 2015, for U.S. Appl. No. 13/168,644, filed Jun. 24, 2011, 16 pages.
Non-Final Office Action dated Jun. 25, 2015, for U.S. Appl. No. 12/457,332, filed Jun. 8, 2009, 7 pages.
Non-Final Office Action dated Jul. 8, 2015, for U.S. Appl. No. 12/457,331, filed Jun. 8, 2009, 13 pages.
Brazzle, J. et al. Active Microneedles with Integrated Functionality, Solid-State Sensor and Actuator Workshop, Hilton Head Island, South Carolina, Jun. 4-8, 2000, Technical Digest, 199-202.
Burge, M.R., (Aug. 2001). "Lack of Compliance with Home Blood Glucose Monitoring Predicts Hospitalization in Diabetes", Diabetes Care 24(8): 1502-1503.
Extended European Search Report dated Apr. 19, 2011, for EP Application No. 10 18 0848.3 filed Sep. 28, 2010, 5 pages.
Extended European Search Report dated Feb. 22, 2012, for EP Application No. EP 10 18 1155, filed Sep. 28, 2010, 6 pages.
Extended European Search Report dated Jan. 22, 2013, for EP Application No. 12182900.6, filed on Sep. 29, 2006, 6 pages.
Extended European Search Report dated Apr. 29, 2013 for EP Patent Application No. 12192620.8, filed on Nov. 14, 2012, 8 pages.
Extended European Search Report dated Nov. 8, 2016, for EP Application No. 16 167 087.2, filed on Aug. 3, 2012, 6 pages.
Extended European Search Report dated Jan. 20, 2017, for EP Application No. 14 813 126.1, filed Jun. 20, 2014, 8 pages.
Final Office Action dated Jul. 9, 2008, for U.S. Appl. No. 11/529,613, filed Sep. 29, 2006, 19 pages.
Final Office Action dated Nov. 23, 2009, for U.S. Appl. No. 11/529,613, filed Sep. 29, 2006, 20 pages.
Final Office Action dated Jan. 21, 2011, for U.S. Appl. No. 11/529,613, filed Sep. 29, 2006, 7 pages.
Final Office Action dated Aug. 15, 2013 for U.S. Appl. No. 13/562,129, filed Jul. 30, 2012, 12 pages.
Final Office Action dated Apr. 13, 2016, for U.S. Appl. No. 13/669,366, filed Nov. 5, 2012, 31 pages.

(56) References Cited

OTHER PUBLICATIONS

Final Office Action dated Aug. 28, 2014, for U.S. Appl. No. 13/562,129, filed Jul. 30, 2012, 11 pages.
Final Office Action dated Dec. 26, 2014, for U.S. Appl. No. 13/669,366, filed Nov. 5, 2012, 9 pages.
Final Office Action dated Jan. 22, 2014, for U.S. Appl. No. 13/669,366, filed Nov. 5, 2012, 8 pages.
Final Office Action dated Jun. 30, 2010, for U.S. Appl. No. 11/529,612, filed Sep. 29, 2006, 11 pages.
Final Office Action dated May 30, 2007, for U.S. Appl. No. 11/125,107, filed May 10, 2005, 11 pages.
Final Office Action dated Nov. 1, 2010, for U.S. Appl. No. 11/311,667, filed Dec. 20, 2005, 9 pages.
Final Office Action dated Nov. 21, 2011, for U.S. Appl. No. 11/311,667, filed Dec. 20, 2005, 8 pages.
Final Office Action dated Jun. 11, 2010, for U.S. Appl. No. 11/529,614, filed Sep. 29, 2006, 16 pages.
Final Office Action dated Mar. 10, 2015, for U.S. Appl. No. 11/529,614, filed Sep. 29, 2006, 24 pages.
Hemmerich, K.J. et al. (Apr. 1995)."Guide to Engineering Thermoplastics," Medical Devices and Diagnostic Industry pp. 39-59.
International Search Report dated Dec. 3, 2004, for PCT Application No. PCT/US2004/08798, filed on Mar. 24, 2004, 3 pages.
International Search Report dated May 2, 2007, for PCT Application No. PCT/US2006/37923, filed on Sep. 9, 2006, 1 page.
International Search Report dated Aug. 16, 2007 for PCT Application No. PCT/US2006/038163, filed on Sep. 29, 2006, 1 page.
International Search Report dated Aug. 17, 2007 for PCT/US2006/38049, filed on Sep. 29, 2006, 1 page.
International Search Report dated Oct. 19, 2012 for PCT Application No. PCT/US2012/049629, filed on Aug. 3, 2012, 4 pages.
Integ. (2000). "LifeGuide™ Glucose Meter. No Lancets. No Blood," located at <http://www.integonline.com>, last visited May 1, 2000, 10 pages.
Ishii H. et al., (Aug. 2001). "Seasonal Variation of Glycemic Control in Type 2 Diabetic Patients", Diabetes Care 24(8):1503.
Massey V. et al. (Aug. 1960). "Studies on the Reaction Mechanism of Lipoyl Dehydrogenase" Biochim. Biophys. Acta 48: 33-47.
Non-Final Office Action dated Dec. 12, 2007, for U.S. Appl. No. 11/529,613, filed Sep. 29, 2006, 13 pages.
Non-Final Office Action dated Apr. 28, 2009, for U.S. Appl. No. 11/529,613, filed Sep. 29, 2006, 21 pages.
Non-Final Office Action dated Jun. 4, 2010, for U.S. Appl. No. 11/529,613, filed Sep. 29, 2006, 23 pages.
Non-Final Office Action dated Mar. 23, 2012, for U.S. Appl. No. 13/197,592, filed Aug. 3, 2011, 7 pages.
Non-Final Office Action dated Mar. 23, 2012, for U.S. Appl. No. 13/197,603, filed Aug. 3, 2011, 6 pages.
Non-Final Office Action dated Nov. 26, 2012 for U.S. Appl. No. 13/562,129, filed Jul. 30, 2012, 9 pages.
Non Final Office Action dated Apr. 8, 2015, for U.S. Appl. No. 13/566,886, filed Aug. 3, 2012, 11 pages.
Non Final Office Action dated Apr. 12, 2011, for U.S. Appl. No. 11/311,667, filed Dec. 20, 2005, 7 pages.
Non Final Office Action dated Aug. 5, 2014, for U.S. Appl. No. 13/669,366, filed Nov. 5, 2012, 8 pages.
Non Final Office Action dated Dec. 5, 2014, for U.S. Appl. No. 13/562,129, filed Jul. 30, 2012, 7 pages.
Non Final Office Action dated Jan. 12, 2009, for U.S. Appl. No. 11/529,612, filed Sep. 29, 2006, 9 pages.
Non Final Office Action dated Jan. 21, 2011, for U.S. Appl. No. 11/529,612, filed Sep. 29, 2006, 9 pages.
Non Final Office Action dated Jul. 13, 2010, for U.S. Appl. No. 12/222,724, filed Aug. 14, 2008, 11 pages.
Non Final Office Action dated Jul. 31, 2015, for U.S. Appl. No. 13/669,366, filed Nov. 5, 2012, 16 pages.
Non Final Office Action dated Mar. 21, 2014, for U.S. Appl. No. 13/562,129, filed Jul. 30, 2012, 12 pages.
Non Final Office Action dated Mar. 25, 2011, for U.S. Appl. No. 12/222,724, filed Aug. 14, 2008, 13 pages.
Non Final Office Action dated Mar. 5, 2010, for U.S. Appl. No. 11/311,667, filed Dec. 20, 2005, 8 pages.
Non Final Office Action dated May 14, 2008, for U.S. Appl. No. 11/529,612, filed Sep. 29, 2006, 9 pages.
Non Final Office Action dated May 16, 2013, for U.S. Appl. No. 13/669,366, filed Nov. 5, 2012, 8 pages.
Non Final Office Action dated May 5, 2005, for U.S. Appl. No. 10/131,268, filed Apr. 23, 2002, 8 pages.
Non Final Office Action dated Nov. 2, 2006, for U.S. Appl. No. 11/125,107, filed May 10, 2005, 10 pages.
Non Final Office Action dated Oct. 14, 2009, for U.S. Appl. No. 11/529,612, filed Sep. 29, 2006, 10 pages.
Non Final Office Action dated Oct. 3, 2008, for U.S. Appl. No. 10/722,074, filed Nov. 24, 2003, 10 pages.
Non-Final Office Action dated Dec. 17, 2015, for U.S. Appl. No. 11/529,614, filed Sep. 29, 2006, 6 pages.
Non Final Office Action dated Dec. 2, 2004, for U.S. Appl. No. 10/347,620, filed Jan. 22, 2003, 8 pages.
Non-Final Office Action dated Jan. 27, 2009, for U.S. Appl. No. 11/529,614, filed Sep. 29, 2006, 17 pages.
Non-Final Office Action mailed on Jan. 6, 2014, for U.S. Appl. No. 11/529,614, filed Sep. 29, 2006, 12 pages.
Non-Final Office Action dated Jun. 21, 2013, for U.S. Appl. No. 13/752,261, filed Jan. 28, 2013, 12 pages.
Non- Final Office Action dated Jun. 6, 2008, for U.S. Appl. No. 11/529,614, filed Sep. 29, 2006, 17 pages.
Non-Final Office Action dated Oct. 9, 2014, for U.S. Appl. No. 14/446,262, filed Jul. 29, 2014, 15 pages.
Non-Final Office Action dated Sep. 29, 2004, for U.S. Appl. No. 10/394,230, filed Mar. 24, 2003, 10 pages.
Notice of Allowance dated May 3, 2011, for U.S. Appl. No. 11/529,613, filed Sep. 29, 2006, 12 pages.
Notice of Allowance dated Mar. 27, 2015, for U.S. Appl. No. 13/562,129, filed Jul. 30, 2012, 7 pages.
Notice of Allowance dated Apr. 18, 2012, for U.S. Appl. No. 11/529,612, filed Sep. 29, 2006, 8 pages.
Notice of Allowance dated Apr. 19, 2010, for U.S. Appl. No. 29/338,117, filed Jun. 4, 2009, 4 pages.
Notice of Allowance dated Aug. 3, 2012, for U.S. Appl. No. 11/529,612, filed Sep. 29, 2006, 5 pages.
Notice of Allowance dated Jan. 14, 2010, for U.S. Appl. No. 29/338,117, filed Jun. 4, 2009, 4 pages.
Notice of Allowance dated Jun. 29, 2012, for U.S. Appl. No. 11/311,667, filed Dec. 20, 2005, 5 pages.
Notice of Allowance dated Mar. 14, 2012, for U.S. Appl. No. 12/222,724, filed Aug. 14, 2008, 7 pages.
Notice of Allowance dated Mar. 31, 2005, for U.S. Appl. No. 10/394,230, filed Mar. 24, 2003, 10 pages.
Notice of Allowance dated May 15, 2008, for U.S. Appl. No. 11/125,107, filed May 10, 2005, 7 pages.
Notice of Allowance dated May 28, 2009, for U.S. Appl. No. 29/300,933, filed May 30, 2008, 6 pages.
Notice of Allowance dated Nov. 23, 2011, for U.S. Appl. No. 12/222,724, filed Aug. 14, 2008, 7 pages.
Notice of Allowance dated Nov. 27, 2012, for U.S. Appl. No. 11/529,612, filed Sep. 29, 2006, 5 pages.
Notice of Allowance dated Nov. 29, 2005, for U.S. Appl. No. 10/131,268, filed Apr. 23, 2002, 6 pages.
Notice of Allowance dated Oct. 12, 2011, for U.S. Appl. No. 11/529,612, filed Sep. 29, 2006, 8 pages.
Notice of Allowance dated Feb. 23, 2015, for U.S. Appl. No. 14/446,262, filed Jul. 29, 2014, 8 pages.
Notice of Allowance dated Feb. 5, 2014, for U.S. Appl. No. 13/752,261, filed Jan. 28, 2013, 9 pages.
Notice of Allowance dated Jun. 15, 2009, for U.S. Appl. No. 10/722,074, filed Nov. 24, 2003, 6 pages.
Notice of Allowance dated Mar. 2, 2016, for U.S. Appl. No. 11/529,614, filed Sep. 29, 2006, 12 pages.
Notice of Allowance dated Mar. 28, 2005, for U.S. Appl. No. 10/347,620, filed Jan. 22, 2003, 6 pages.
Notice of Allowance dated Jan. 26, 2017, for U.S. Appl. No. 12/457,331, filed Jun. 8, 2009, 7 pages.

(56) References Cited

OTHER PUBLICATIONS

Sonntag, O. (1993). Ektachem. Dry Chemistry, Analysis With Carrier-Bound Reagents, Elsevier Science Publishers, 57 pages.
Spielman, a. et al. (2001). *Mosquito: A Natural History of Our Most Persistent and Deadly Foe*, First Edition, Hyperion, New York, NY, 3 pages. (Table of Contents Only).
Straub F.B. (Mar., 1939). "Isolation and Properties of a flavoprotien from Heart Muscle Tissue", Biochemical Journal 33: 787-792.
U.S. Precision Lens, Inc. (1983).The Handbook of Plastic Optics.
Written Opinion dated Dec. 3, 2004, for PCT Application No. PCT/US2004/08798, filed on Mar. 24, 2004, 4 pages.
Written Opinion dated May 2, 2007, for PCT Application No. PCT/US2006/37923, filed on Sep. 9, 2006, 5 pages.
Written Opinion dated Aug. 17, 2007 for PCT/US2006/38049, filed on Sep. 29, 2006, 6 pages.
Written Opinion dated Aug. 16, 2007 for PCT Application No. PCT/US2006/038163, filed on Sep. 29, 2006, 4 pages.
Written Opinion dated Oct. 19, 2012 for PCT Application No. PCT/US2012/049629, filed on Aug. 3, 2012, 7 pages.
Final Office Action dated Feb. 8, 2017, for U.S. Appl. No. 12/457,332, filed Jun. 8, 2009, 11 pages.
Clarke, W.L. et al. (1981). "Evaluation of a New Reflectance Photometer for Use in Home Blood Glucose Monitoring," *Diabetes Care* 4(5):547-550.
Restriction Requirement dated Sep. 29, 2011, for U.S. Appl. No. 12/457,332, filed Jun. 8, 2009, 6 pages.
Restriction Requirement dated Dec. 22, 2011, for U.S. Appl. No. 12/457,332, filed Jun. 8, 2009, 6 pages.
Tietz, N.W. (1986).Textbook of Clinical Chemistry, W. B. Saunders Company, pp. 1533 and 1556.
Extended European Search Report dated Jul. 18, 2013, for EP Application No. 06 772 943.4, filed on Jun. 13, 2006, 7 pages.
Extended European Search Report dated Aug. 27, 2012, for EP Application No. 09 758 789.3, filed on Jun. 8, 2009, 13 pages.
Extended European Search Report dated Oct. 27, 2016, for EP Application No. 11 798 518.4, filed on Jun. 24, 2011, 7 pages.
Final Office Action dated Jan. 20, 2016, for U.S. Appl. No. 12/457,332, filed Jun. 8, 2009, 10 pages.
Final Office Action dated May 5, 2016, for U.S. Appl. No. 12/457,331, filed Jun. 8, 2009, 11 pages.
Final Office Action dated Aug. 12, 2016, for U.S. Appl. No. 13/168,644, filed Jun. 24, 2011, 18 pages.
Final Office Action dated Oct. 15, 2009, for U.S. Appl. No. 11/239,122, filed Sep. 30, 2005, 13 pages.
Final Office Action dated Aug. 14, 2012, for U.S. Appl. No. 13/037,089, filed Feb. 28, 2011, 14 pages.
Final Office Action dated Sep. 23, 2013, for U.S. Appl. No. 13/037,089, filed Feb. 28, 2011, 14 pages.
International Search Report dated Jan. 16, 2008, for PCT Application No. PCT/US2006/022840, filed on Jun. 13, 2006, 1 page.
Non-Final Office Action dated Mar. 19, 2009, for U.S. Appl. No. 11/239,122, filed Sep. 30, 2005, 15 pages.
Non-Final Office Action dated Sep. 1, 2010, for U.S. Appl. No. 11/239,122, filed Sep. 30, 2005, 15 pages.
Non-Final Office Action dated Sep. 13, 2011, for U.S. Appl. No. 13/037,089, filed Feb. 28, 2011, 14 pages.
Non-Final Office Action dated Feb. 28, 2013, for U.S. Appl. No. 13/037,089, filed Feb. 28, 2011, 12 pages.
Non-Final Office Action dated Apr. 10, 2014, for U.S. Appl. No. 13/037,089, filed Feb. 28, 2011, 14 pages.
Non-Final Office Action dated May 29, 2015, for U.S. Appl. No. 14/614,177, filed Feb. 4, 2015, 13 pages.
Notice of Allowance dated Sep. 18, 2014, for U.S. Appl. No. 13/037,089, filed Feb. 28, 2011, 9 pages.
Notice of Allowance dated Feb. 16, 2016, for U.S. Appl. No. 14/614,177, filed Feb. 4, 2015, 7 pages.
Written Opinion of the International Searching Authority dated Jan. 16, 2008, for PCT Application No. PCT/US2006/022840, filed on Jun. 13, 2006, 3 pages.
Final Office Action dated Jun. 12, 2018, for U.S. Appl. No. 15/499,821, filed Apr. 27, 2017, 12 pages.
Notice of Allowance dated May 18, 2009, for U.S. Appl. No. 29/300,934, filed May 30, 2008, 4 pages.
Non-Final Office Action dated Mar. 20, 2019, for U.S. Appl. No. 15/499,821, filed Apr. 27, 2017, 12 pages.
Non-Final Office Action dated Mar. 27, 2019, for U.S. Appl. No. 12/457,332, filed Jun. 8, 2009, 8 pages.
Notice of Allowance dated May 15, 2019, for U.S. Appl. No. 12/457,332, filed Jun. 8, 2009, 8 pages.
Notice of Allowance dated Feb. 4, 2019, for U.S. Appl. No. 13/168,644, filed Jun. 24, 2011, 9 pages.
Final Office Action dated Nov. 25, 2019, for U.S. Appl. No. 15/499,821, filed Apr. 27, 2017, 13 pages.
Extended European Search Report dated Feb. 26, 2020, for European Application No. 19196465.9, filed on Jun. 8, 2009, 6 pages.
Wikipedia (2016). "Capillary action," 7 pages.
Non-Final Office Action dated Dec. 16, 2016, for U.S. Appl. No. 13/566,886, filed Aug. 3, 2012, 11 pages.
Final Office Action dated Sep. 21, 2017, for U.S. Appl. No. 13/168,644, filed Jun. 24, 2011, 14 pages.
Non-Final Office Action dated Mar. 20, 2017, by the United States Patent and Trademark Office for U.S. Appl. No. 15/191,434, filed Jun. 23, 2016, 20 pages.
Non-Final Office Action dated May 15, 2017, by the United States Patent and Trademark Office for U.S. Appl. No. 14/743,867, filed Jun. 18, 2015.
Notice of Allowance dated Aug. 18, 2017, for U.S. Appl. No. 13/566,886, filed Aug. 3, 2012, 10 pages.
Non-Final Office Action dated Mar. 21, 2017, for U.S. Appl. No. 15/177,041, filed Jun. 8, 2016, 11 pages.
Non-Final Office Action dated Sep. 29, 2017, for U.S. Appl. No. 15/499,821, filed Apr. 27, 2017, 10 pages.
Final Office Action dated Nov. 29, 2017, for U.S. Appl. No. 15/177,041, filed Jun. 8, 2016, 13 pages.
Final Office Action dated Mar. 28, 2018, for U.S. Appl. No. 12/457,332, filed Jun. 8, 2009, 13 pages.

* cited by examiner

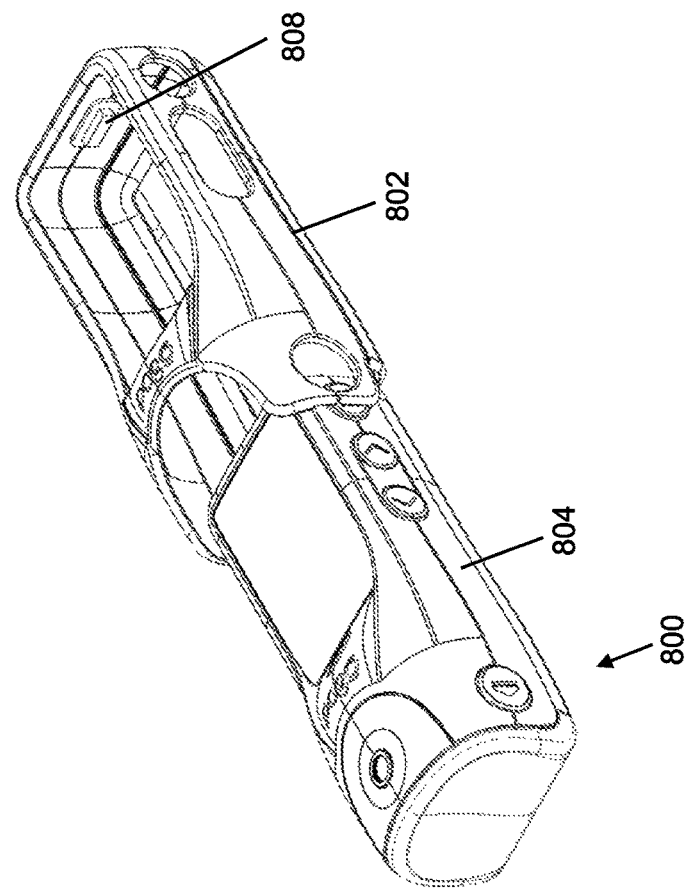
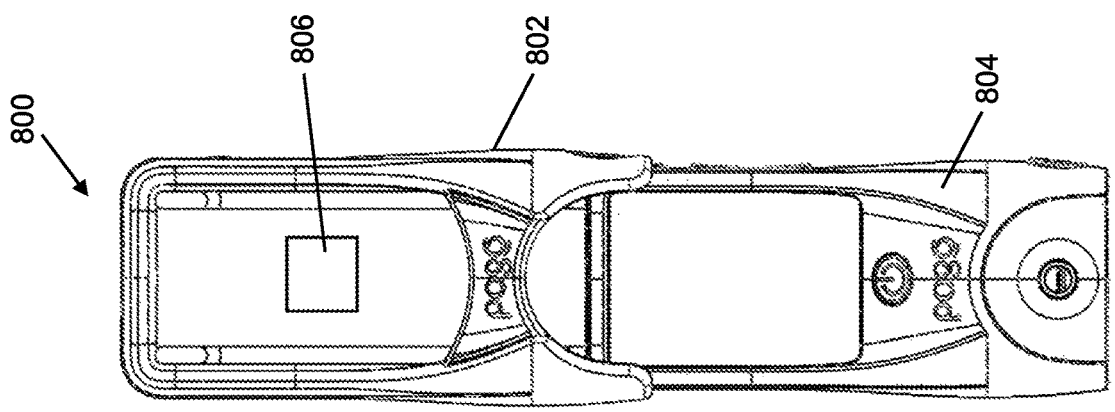
FIG. 8B
FIG. 8A

ANALYTE MONITORING SYSTEM WITH AUDIBLE FEEDBACK

CROSS-REFERENCE TO RELATED APPLICATIONS

This application claims priority to U.S. Provisional Application Ser. No. 61/838,171, filed on Jun. 21, 2013, which is hereby incorporated by reference in its entirety.

FIELD

The present invention relates to devices and methods for monitoring an analyte in a fluid sample (e.g. blood glucose) and providing visual and/or auditory feedback to a user of the devices.

BACKGROUND

Diabetes is a widespread condition, affecting millions worldwide. In the United States alone, an estimated 23.6 million people, or 7.8% of the population, have the condition. Diabetes accounts for an estimated $174 billion annually in direct and indirect medical costs. Depending on the type (Type 1, Type 2, and the like), diabetes may be associated with one or more symptoms such as fatigue, blurred vision, and unexplained weight loss, and may further be associated with one more complications such as hypoglycemia, hyperglycemia, ketoacidosis, neuropathy, and nephropathy.

To help delay or prevent these undesirable complications, it may be necessary for people with diabetes to monitor one or more blood analyte levels, such as blood glucose. Glucose testing allows a patient to ensure that his or her blood glucose is at a safe level, which in turn may help monitor the effectiveness of diet, medication, and exercise in controlling the patient's diabetes, and may also help reduce the risk of developing one or more diabetes-related conditions (e.g., blindness, kidney damage and nerve damage). Many of the currently available glucose meters, however, require numerous components and complicated steps to complete a test, and may result in a frustrating or otherwise negative user experience (which may reduce the likelihood of user compliance). As such, it may be desirable to produce safe and effective analyte concentration meters that may make sampling discrete and easier for the user.

BRIEF SUMMARY

Described here are analyte measurement devices and systems for providing feedback to a user. In some variations, an analyte measurement device may be configured to produce a plurality of auditory prompts to a user, and these prompts may convey information, instructions, and/or encouragement to a user. In some variations, the analyte measurement device may be able to change a set of auditory prompts outputted by the analyte measurement device. In some of these variations, a system may comprise an analyte measurement device comprising a housing, a speaker and a control unit. In these variations, the housing may comprise a releasable housing portion and the releasable housing portion may comprise an auditory identifier that is associated with an auditory prompt set. The control unit may be configured to detect the auditory identifier, set the auditory prompt set associated with the detected auditory identifier as an active prompt set, and instruct the speaker to output at least one auditory prompt from the active prompt set. In some variations, the control unit may comprise a processor and/or a memory unit.

In some variations the system may further comprise a plurality of releasable housing portions. In some of these variations, each of the releasable housing portions may be associated with an auditory prompt set comprising at least one auditory prompt that differs from at least one auditory prompt associated with the other releasable housing portions of the plurality of releasable housing portions. In some embodiments, the auditory prompt set associated with a releasable housing portion may be stored on the memory unit. In other embodiments, the auditory prompt set associated with the releasable housing portion may be stored on the releasable housing portion or on a server. The control unit may also comprise a speech unit and instructing the speaker to output at least one auditory prompt from the active prompt set may comprise transmitting a signal associated with the at least one auditory prompt from the speech unit to the speaker. In some variations, the analyte measurement devices described here may further comprise a display and/or a microphone. In some embodiments, the analyte measurement device may be an integrated meter. In some variations, the system may further comprise a cartridge.

In some embodiments, a system may comprise an analyte measurement device comprising a housing, a speaker, a control unit, and a skin. In these variations, the skin may be configured to releasably attach to the housing and may comprise an auditory identifier that may be associated with an auditory prompt set. The control unit may be configured to detect the auditory identifier, set the auditory prompt set associated with the detected auditory identifier as an active prompt set, and instruct the speaker to output at least one auditory prompt from the active prompt set. In some variations, the control unit may comprise a processor and/or a memory unit.

In some variations the system may further comprise a plurality of skins. In some of these variations, each skin may be associated with an auditory prompt set comprising at least one auditory prompt that differs from at least one auditory prompt associated with the other skins of the plurality of skins. In some embodiments, the auditory prompt set associated with a skin may be stored on the memory unit. In other embodiments, the auditory prompt set associated with the skin may be stored on the skin or on a server. The control unit may also comprise a speech unit and instructing the speaker to output at least one auditory prompt from the active prompt set may comprise transmitting a signal associated with the at least one auditory prompt from the speech unit to the speaker. In some variations, the analyte measurement devices described here may further comprise a display and/or a microphone. In some embodiments, the analyte measurement device may be an integrated meter. In some variations, the system may further comprise a cartridge.

BRIEF DESCRIPTION OF THE DRAWINGS

FIGS. 8A and 8B depict a front view and perspective view respectively of a variation of the analyte measurement devices described here with a skin.

DETAILED DESCRIPTION

Figure 1C:
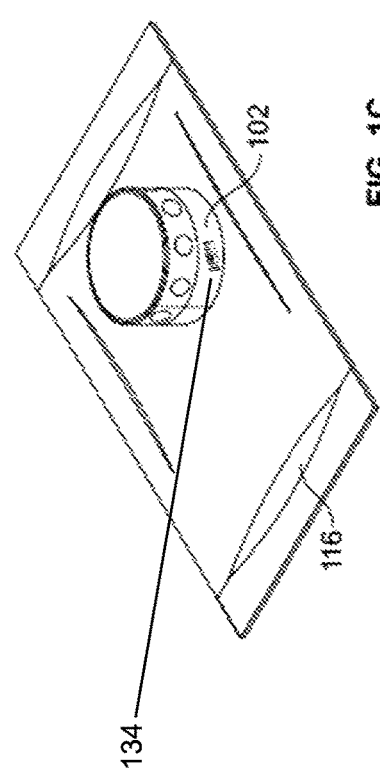
FIG. 1C depicts a perspective view of a cartridge that may be used with an analyte measurement device described here.

Described here are analyte measurement systems and devices, and methods of using the same. Generally, the devices described here comprise an analyte measurement device configured to audibly communicate with a user. In some embodiments, the analyte measurement devices audibly and/or visually communicate with the user by outputting prompts or receiving commands. In some variations, the analyte measurement devices may be configured with an auditory and/or visual output based on one or more removable components of the analyte measurement device. In these variations, the systems may comprise an analyte measurement device and one or more removable components (e.g., a removable portion of a housing, a cartridge, a skin, or the like).

Analyte Measurement Devices

Generally, the analyte measurement devices described here are configured to perform one or more steps of an analyte measurement operation in which the concentration of one or more analytes in a fluid sample is measured. For example, an analyte measurement device may be configured to perform one or more of the following operations: collect a fluid sample from a sampling site, transport the fluid sample to an analysis site, and analyze the fluid sample. When the analyte measurement device is configured to collect a fluid sample from a sampling site, the device may be configured to collect a fluid sample from any suitable sampling site. Examples of suitable sampling sites include, but are not limited to, one or more body sites (e.g., fingers, toes, other skin surfaces, or the like) or one or more artificial containers (e.g., a vial holding a control solution or a body fluid sample). The fluid sample may comprise any suitable fluid, such as, for example, one or more solutions (e.g., a control solution), mixtures, body fluids (e.g., blood, saliva, or the like), combinations thereof and the like. Analysis of a fluid sample may include determining the concentration of one or more analytes in the sample, such as one or more hormones, proteins, enzymes, toxins, drugs, other molecules, or the like. In some variations, the analyte measurement devices described here may be configured to measure the glucose concentration of one or more blood samples or other glucose-containing solutions.

In some variations, an analyte measurement device as described here may be fully integrated, in that the device may contain all of the components necessary for collecting, transporting, and analyzing a fluid sample. For example, the systems described here may comprise one or more of the devices described in U.S. patent application Ser. No. 13/566,886, filed Aug. 3, 2012 and titled "DEVICES AND METHODS FOR BODY FLUID SAMPLING AND ANALYSIS," U.S. Pat. No. 7,004,928, filed Apr. 23, 2002 and titled "AUTONOMOUS, AMBULATORY ANALYTE MONITOR OR DRUG DELIVERY DEVICE," and U.S. Pat. No. 8,012,103 and titled "CATALYSTS FOR BODY FLUID SAMPLE EXTRACTION," the contents of each of which are hereby incorporated by reference in their entirety. It should also be appreciated that the analyte measurement devices described here may be configured to perform only a subset of the collecting, transporting, and analyzing operations associated with analysis of a fluid sample.

For example, the analyte measurement device may comprise a fully integrated meter. The meter may comprise a meter housing and one or more cartridges, which will be described in more detail below. In some variations, the meter may be configured to collect and analyze a plurality of fluid samples. For example, in some variations, a cartridge may comprise one or more cells, some or all of which may contain one or more sampling arrangements for collecting a fluid sample, as described in more detail below. The meter may be further configured to audibly, visually or otherwise provide one or more results from the sample analysis. Some portions of the meter may be reusable, while other portions of the meter may be disposable. For example, in some variations, the meter housing is reusable while the cartridge is disposable. In these variations, new cartridges may be inserted into or otherwise engage with a meter housing to conduct a new series of tests. In other variations, both the meter housing and the cartridge may be disposable.

Figure 1B:
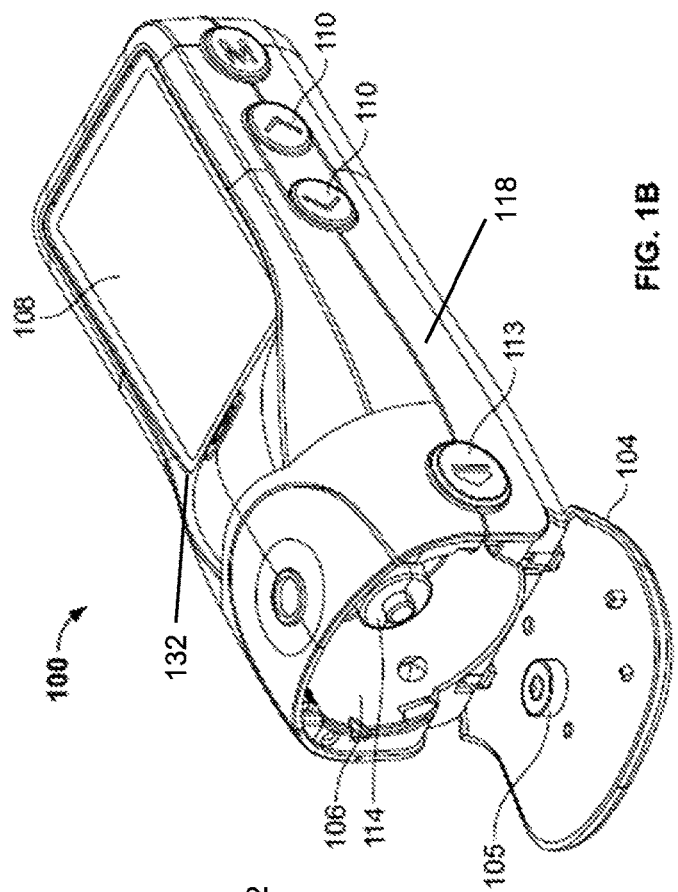
FIGS. 1A-1B depict a front view, and a perspective bottom view, respectively of a variation of an analyte measurement device as described here.
Figure 1A:
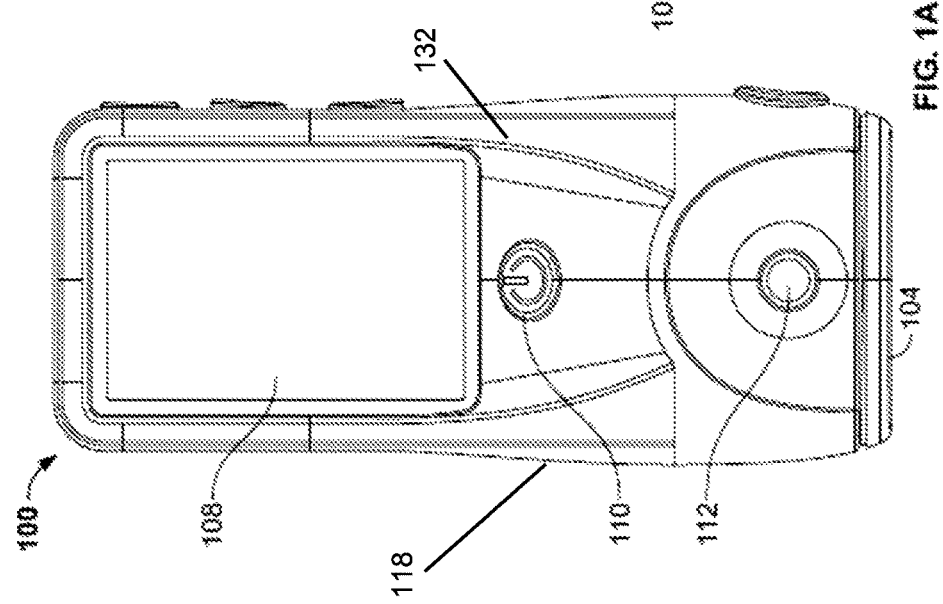

FIGS. 1A-1C show an illustrative variation of an exemplary integrated meter (100). Specifically, FIGS. 1A and 1B show a front view and a bottom perspective view, respectively, of a meter housing (118), while FIG. 1C shows a perspective view of the cartridge (102). While shown in FIG. 1C as being stored in a sealed or sealable pouch (116), the cartridge (102) may be stored in any suitable container, and may be removed prior to use. As shown in FIGS. 1A and 1B, the meter housing (118) may comprise a door (104) with a cartridge-engagement projection (105), a cartridge-receiving chamber (106) or cavity, a cartridge ejection button (113), a display (108), buttons (110), a port (112), and a tower (114). The meter need not include each of these features, and it should be appreciated that the meter may comprise any combination of these features. The meter (100) may further comprise one or more imaging systems (not shown), and internal mechanisms or components (e.g., memory, circuitry, actuators, batteries, vacuum pumps, sensors, combinations thereof, etc.) for operating the meter and/or facilitating a testing procedure.

A cover or door (104) may be opened to reveal a cartridge-receiving chamber (106), as shown in FIG. 1B. A cartridge (102) may be placed inside of cartridge-receiving chamber (106), and the door (104) may be closed to temporarily enclose the cartridge (102) within the meter housing (118). When placed inside of the meter housing, one or more portions of the cartridge (102) may engage one or more components of the meter housing (118). In some variations, the meter housing (118) may comprise one or more features that may facilitate self-alignment of the cartridge (102) as it is placed in the cartridge-receiving chamber (106). For example, in some variations the cartridge (102) may comprise a recess (not shown). When the cartridge (102) is placed inside of the cartridge-receiving chamber (106), a portion of the tower (114) may fit within or otherwise engage the recess of the cartridge (102). This engagement may help to hold the cartridge (102) in place relative to meter housing (118). Conversely, in some variations, the cartridge (102) may comprise one or more projections (not shown) that may engage one or more recesses (not shown) in the cartridge-receiving chamber (106) or other portion of the meter housing (118). Additionally or alternatively, one or more magnets may hold the cartridge in place relative to the meter housing. A cartridge need not be placed inside of a meter housing (e.g., via a cartridge-receiving chamber) to engage the meter housing. For example, in some variations, a cartridge may attach to or otherwise engage one or more external surfaces of a meter housing.

Any suitable cartridge may be used with the meters. For example, in some variations, the meter may comprise one or more of the cartridges described in U.S. patent application Ser. No. 11/529,614, titled "MULTI-SITE BODY FLUID SAMPLING AND ANALYSIS CARTRIDGE," and U.S. Pat. No. 8,231,832, titled "ANALYTE CONCENTRATION DETECTION DEVICES AND METHODS," the contents of each of which is hereby incorporated by reference in its entirety. A suitable variation of a cartridge that may be used with the meter described above is illustrated in FIG. 2A. As shown there, the cartridge (200) may house or otherwise hold one or more sampling arrangements (202). These sampling arrangements (202) may comprise one or more components for collecting, transporting, and/or reacting with a fluid sample. For example, in some variations, the sampling arrangement may comprise a penetration member for piecing, penetrating or otherwise puncturing a sampling site during a testing procedure. In variations where the cartridge (200) comprises a plurality of sampling arrangements (202), each sampling arrangement (202) may be utilized to conduct a separate test on a different fluid sample. The sampling arrangement may further comprise a hub or other structure for moving the penetration member relative to the cartridge. Additionally, the sampling arrangement (202) may comprise a quantification member (not shown), which may react with the fluid sample to produce a measurable response (e.g., an electrochemical or photometric response) that may be indicative of one or more properties of the fluid sample. In variations where the cartridge (200) is configured to be disposable, new cartridges may be swapped in to provide unused (e.g., unfired) sampling arrangements. Any reactions that occur between sampling arrangement and the fluid sample may be quantified or measured by one or more portions of the cartridge or the meter housing (e.g., an imaging system). In some variations, one or more portions of the cartridge may be reusable. For example, a cartridge containing one or more unused sampling arrangements may be loaded into the cartridge to allow the meter to conduct additional testing procedures. While the meter (100) is discussed above as having a cartridge, the meter need not.

Figure 2B:
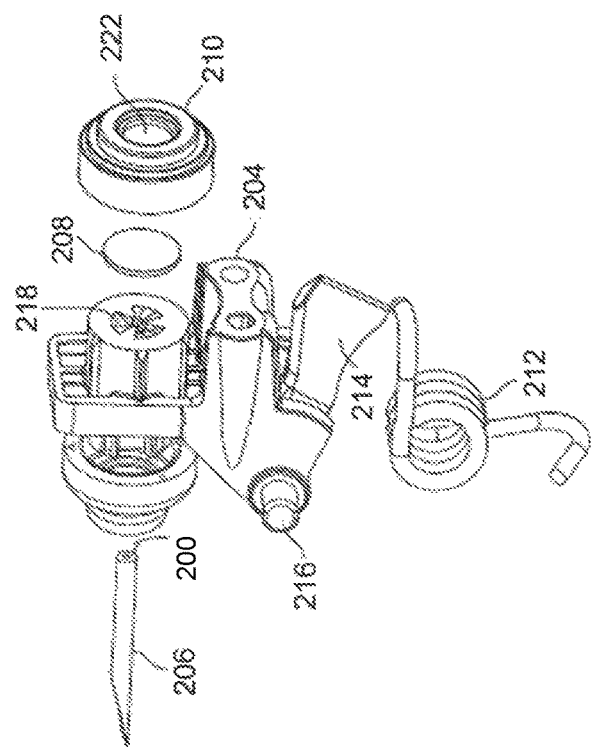
FIG. 2B depicts an exploded view of a sampling arrangement contained in a cartridge.
Figure 2A:
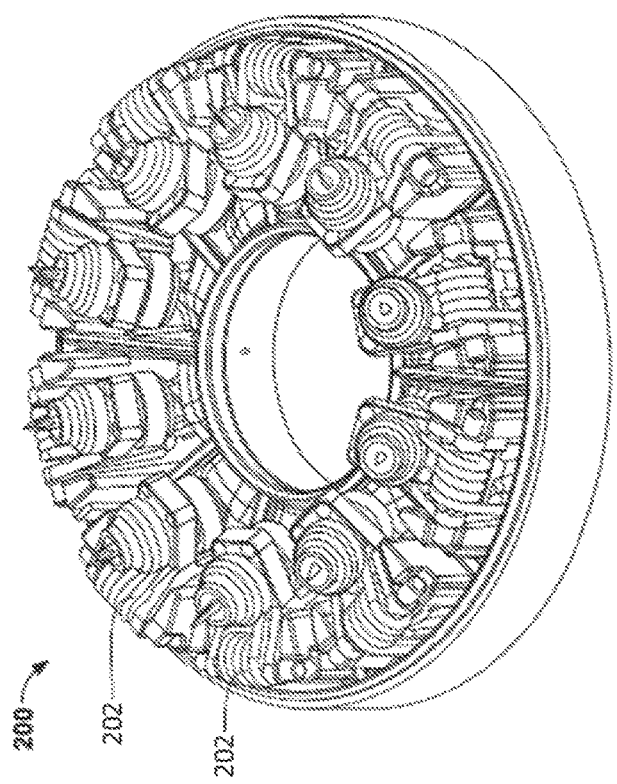
FIG. 2A depicts a perspective view of a cartridge.

FIG. 2B depicts an exploded view of a sampling arrangement (202). Shown there are a hub (204), a skin penetration member (206), a quantification member (208) (e.g., a pad), a cap (210), and a spring (212). The hub (204) may comprise a latch (214), pivot bars (216), and a micropatterned surface (218). In this variation, the hub (204) may hold the skin penetration member (206) such that an interior bore (220) of the skin penetration member (206) is in fluid communication with the micropatterned surface (218). The quantification member (208) may be placed on the micropatterned surface (218) and a cap (210) may be placed at least partially over the quantification member (208) to hold the quantification member (208) in place against the micropatterned surface (218). The cap (210) may comprise an aperture (222) through which the quantification member (208) may be viewed by an imaging system (e.g., light source and detector) to determine the concentration of an analyte in a sample. While spring (212) is depicted as a torsional spring, any mechanism capable of moving the skin penetration member may be utilized (e.g., linear spring, leaf spring, conical spring, mechanically-driven arm, sliding actuator etc.).

The meter housing (118) may be configured to house a speaker and/or a microphone (not shown) and a control unit (not shown), although it should be appreciated that the speaker, microphone, and/or control unit may in some instances be partially housed in the housing (118), may be externally attached to the housing (118), or may be part of a separate device (i.e., headphones, cellular phone, computer, tablet, etc.) that communicates with the meter either wirelessly or through a wired connection. As depicted in FIG. 1A, the meter housing (118) may additionally comprise a display (108) (e.g., for visually providing information to a user), buttons (110) (e.g., for powering on/off the device, inputting information into the device, etc.) and a port (112) (e.g., through which a fluid sample may be collected), such as those described in U.S. patent application Ser. No. 13/566,886, which was previously incorporated by reference in its entirety. Additionally or alternatively, the meter (100) may in some instances further comprise one or more imaging systems (not shown), and internal mechanisms or components (e.g., memory, circuitry, actuators, batteries, vacuum pumps, sensors, combinations thereof, etc.) for operating the meter (100) and/or facilitating testing of a fluid sample The analyte measurement devices described here need not include each of these features, and variations of these devices may comprise any combination of these features.

As mentioned above, the analyte measurement devices described here are generally configured to provide some form of feedback (auditory, visual, tactile, etc.) to a user. Generally, the analyte measurement devices described here may comprise a control unit comprising a memory unit (which can include one or more computer-readable storage mediums), one or more processors (CPU's), and a speech unit. The one or more processors may execute various software programs and/or sets of instructions stored in the memory unit to perform various functions for the device and to process data. In some examples, the memory unit, processor and speech unit may be implemented on a single chip. In other examples, they can be implemented on separate chips. Depending on the desired functionality of the device, the device may further comprise any number of components, including but not limited to, circuitry of any kind (e.g., RF circuitry, audio circuitry, display circuitry, lighting circuitry, integrated circuits, etc.), a speaker, a microphone, a tactile output generator (e.g., a vibrational element), a display (including a touch-sensitive display system), one or more external ports, etc. The device may include all of the above listed components, or any sub combination of the components. Additionally, the various components described may be implemented across two or more devices (e.g., an analyte measurement device and a cellular phone), of which one or more may include a home computer, or a remote server accessed by a local area network or by the internet. In an example where two or more devices are used, the devices can communicate with each other to facilitate operation of the devices. The communication may or may not be encrypted.

The analyte measurement devices may also be configured to receive, compile, store, and access data. In some variations, the analyte measurement device may be configured to access and/or receive data from different sources. The analyte measurement device may be configured to receive data directly entered by a user and/or it may be configured to receive data from separate devices (e.g. a cellular phone, tablet, computer, etc.) and/or from a storage medium (flash drive, memory card, etc.). The analyte measurement device may receive the data through a network connection, as discussed in more detail below, or through a physical connection with the device or storage medium (e.g. through USB or any other type of port). The analyte measurement device may compile the data using a processor and may store the data on a memory unit within the access device, or it may transmit the data to an external server for storage. Furthermore, the analyte measurement device may later access the stored data using the processor.

The analyte measurement device may be configured to receive various types of data. For example, the analyte measurement device may be configured to receive a user's personal data (e.g., gender, weight, birthday, age, height, diagnosis date, anniversary date using the device, etc.), a user's testing history (e.g., number of tests completed, time each test was completed, date each test was completed, pre or post prandial test markings, how many tests a user has completed consecutively, etc.), a user's results history (e.g., glucose level at time test was taken), a user's diet information (e.g., what a user had to eat each day, number of alcoholic beverages, amount of carbohydrates consumed, etc.), a user's exercise information (e.g., if a user exercised, when the user exercised, duration of exercise, what type of exercise the user completed (e.g. biking, swimming, running, etc.), exertion level of the exercise (e.g., low, medium, high), a user's heart rate during exercise, etc.), general health information of other similarly situated patients (e.g., typical test results for a similar user at a similar time of day, average of test results for a similar user after exercise, etc.), or any other information that may be relevant to a user's treatment. In some variations, the analyte measurement device may be configured to create, receive, and/or store user profiles. A user profile may contain any of the user specific information previously described. Additionally, the analyte measurement device may be configured to receive general information useful in determining when testing occurs (e.g., time of day, date, location) as is described in more detail in U.S. patent application Ser. No. 12/457,332, titled "MEDICAL DIAGNOSTIC DEVICES AND METHODS," the content of which is hereby incorporated by reference in its entirety. While the above mentioned information may be received by the analyte measurement device, in some embodiments the analyte measurement device may be configured to calculate any of the above data from information it has received using software stored on the device itself, or externally.

In some embodiments, the analyte measurement device may be configured to identify patterns in user behavior, use the identified patterns to predict future user behavior, and provide prompts to the user relating to the identified patterns, as is described in more detail in U.S. patent application Ser. No. 12/457,332, titled "MEDICAL DIAGNOSTIC DEVICES AND METHODS," which was previously incorporated by reference in its entirety. In some instances, the analyte measurement device may use the patterns to help warn about, or prevent the occurrence of one or more glucose events. A glucose event may occur any time a user's glucose is above or below an expected level or is outside a specified range. In some embodiments, a glucose event may be a hypoglycemic event or a hyperglycemic event. In some variations, the analyte measurement device may be configured to compare the user's personal data, testing history, diet information, exercise information, or any other relevant information, to a user's historical data (e.g. prior test data, user's historical trends, etc.), data preloaded onto the analyte measurement device that has been compiled from external sources (e.g. medical studies), or data received from a separate device (e.g., historical data or data compiled from external sources), as is described in more detail below. In some instances, the warning or notification may include instructions to perform a test, seek medical attention, and/or to eat or drink something.

The analyte measurement device may be configured to calculate the likelihood of a glucose event based on data it has received and may provide an alert or prompt to a user based on its calculation. In some variations, the method of alerting a user of a glucose event may comprise receiving user information, identifying the user information as a stimulus for a glucose event (e.g., exercise, alcohol consumption, sugar consumption, heavy meals, etc.), calculating a likelihood of occurrence of the glucose event, determining when the glucose event will occur, and alerting or prompting the user in advance of the glucose event based on the determination of when the glucose event will occur. The reporting of a risk, if any, may be based upon whether the risk calculation meets or exceeds a certain threshold, or certain criteria.

For example, some users may experience a higher risk of a glucose event after intense exercise (e.g., high intensity for 60 minutes, moderate intensity for 90 minutes, low intensity for 120 minutes) or after consuming a certain number or amount of alcoholic beverages (e.g. 5 glasses of wine, 4.5 ounces of vodka, etc.). The user may input information about his exercise regimen or alcohol consumption into the analyte measurement device or a separate device communicating with the analyte measurement device. The analyte measurement device may identify the information as a stimulus for a glucose event based on data preloaded onto the analyte measurement device, data received from a separate device, and/or a user's historical data, and may mark the information as a stimulus. The analyte measurement device may compare the user's information to the preloaded, received, and/or historical data to calculate a likelihood of occurrence of the glucose event. If there is a high probability that a glucose event may occur, the analyte measurement device may use the preloaded, received, and/or historical data to determine when the event is likely to occur (e.g., 12 hours after exercising, 4 hours after consuming alcohol, etc.), and may alert or prompt the user at an appropriate time (e.g., 11 hours after exercising, 3 hours and 45 minutes after consuming alcohol, etc.), as is described in more detail below.

In some embodiments, calculating the likelihood of the occurrence of a glucose event may comprise comparing the user's information with the user's historical information (e.g. prior test result, historical average, historical trend, predictive value, etc.) assigning a probability of a glucose event occurring based on the comparison, determining if the probability is larger than a threshold value, and if so, determining that alerting or prompting a user is necessary. In other embodiments, calculating the likelihood of the occurrence of a glucose event may comprise comparing the user's information with the health information of other patients, for example, similarly situated patients (e.g., patients of similar age, weight, patterns, etc.). In yet other embodiments, calculating the likelihood of the occurrence of a glucose event may comprise comparing the user's information with both the user's historical information and the health information of similarly situated patients, assigning a probability to each comparison, and averaging the probabilities. While a simple average is described, a more complex weighting scheme may be utilized. For example, in some embodiments, the comparison of the user's information with the user's historical information may be weighted more heavily than the comparison of the user's information with the health information of similarly situated patients. In still other variations, calculating the likelihood of the occurrence of a glucose event may comprise comparing many different factors (e.g., duration of exercise, intensity of exercise, last meal, and age) with the same factors in multiple data sets (e.g., historical data, similarly situated patient data, etc.) and assigning each factor a different weight to determine a final probability.

In some examples, determining when the glucose event will occur may also comprise comparing the user's information with the user's historical information or the health information of similarly situated patients. This comparison may provide information about how much time may elapse between the stimulus and the glucose event (i.e. a response time). The response times may also be averaged or assigned weights.

Figure 3B:
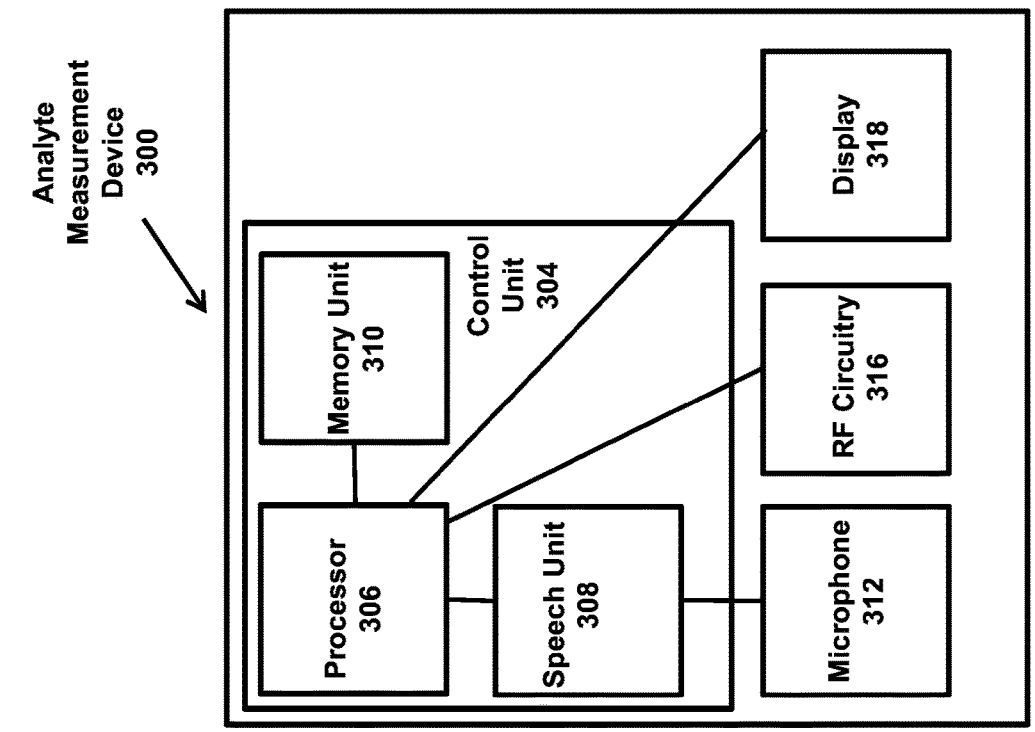
FIGS. 3A and 3B depict block diagrams of variations of the analyte measurement devices described here.
Figure 3A:
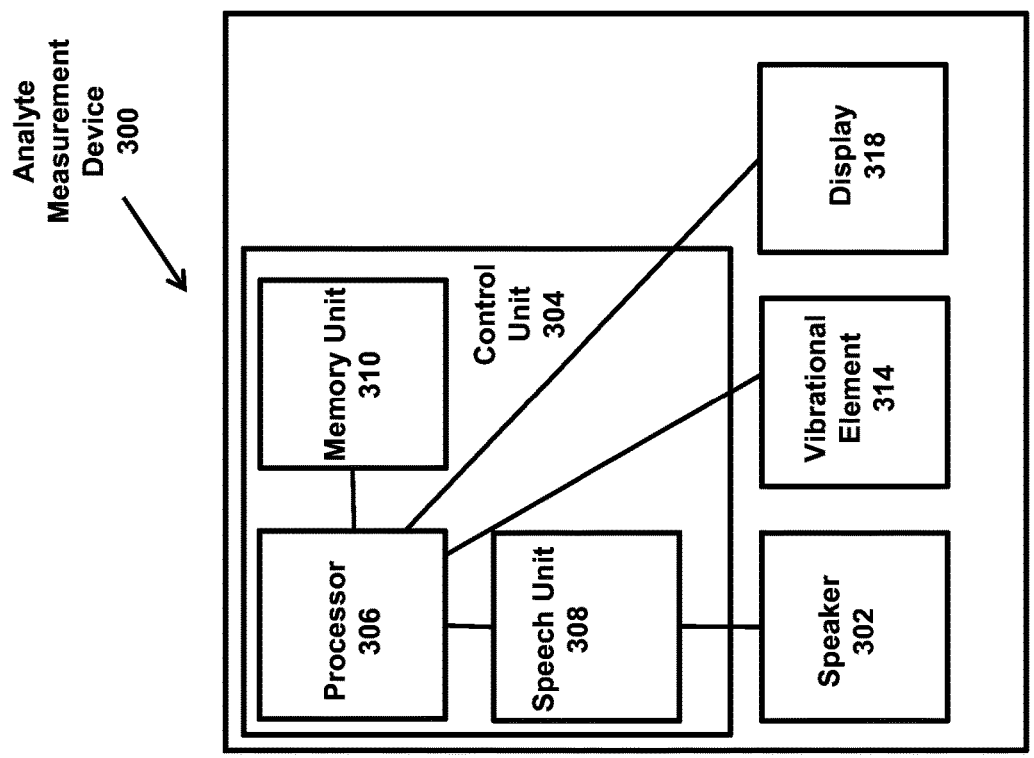

FIGS. 3A and 3B show block diagrams of variations of another analyte measurement device (300). As shown in FIG. 3A, the analyte measurement device (300) may comprise a speaker (302) configured to produce a sound output, and a control unit (304) configured to control the sound output of the speaker (302). The control unit (304) may include electronics capable of outputting audio signals to the speaker (302). For example, in the variations shown in FIGS. 3A and 3B, the control unit (304) may comprise a processor (306), a speech unit (308), and a memory unit (310). The memory unit (310) can include high-speed random access memory and non-volatile memory, such as one or more magnetic disk storage devices, flash memory devices, or other non-volatile solid-state memory devices. In the variation depicted in FIG. 3A, the memory unit (310) may be configured to store data relating to a plurality of sound outputs for the speaker (302), the processor (306) may be configured to select a specific sound output from the plurality of sound outputs, and the speech unit (308) may be configured to convert the data relating to the sound output into a signal that may be transmitted to the speaker (302), or a wireless audio transmitter, e.g. IR, Bluetooth, wireless USB protocol, WiFi IEEE 802.11x protocols, 2.4 GHz or 5 GHz transmissions. The speaker (302) may then convert the signal to human-audible sound waves. The data relating to the sound output may comprise any audio file, for example, sample sound files, a library of sounds, recorded data files, sound files that may be used together to form composite speech, or any other type of audible indicia file. In some variations, the analyte measurement device (300) may include a headset jack instead of, or in addition to, a speaker (302). The headset jack may provide an interface between the speech unit (308) and removable audio output devices, such as output-only headphones, an external speaker, or a headset with both an output (e.g. a headphone for one or both ears) and an input (e.g., a microphone.)

In some variations, the analyte measurement device (300) may also comprise a vibrational element (314), for example, a vibrating motor or the like, such that the analyte measurement device may provide tactile feedback to a user. The tactile feedback may be provided to the user through the housing (118), the port (112), or any other component of the device capable of transmitting vibration. In this variation, the memory unit (310) may be configured to store data relating to a plurality of vibrational patterns, and the processor (306) may be configured to select a specific pattern from the plurality of vibrational patterns and communicate with an actuator configured to activate and deactivate the vibrational element.

In some variations, the analyte measurement device (300) may also be configured to produce a visual output to communicate information to a user. As shown in FIG. 3A, the analyte measurement device (300) may comprise a display (318) configured to produce a visual output, and a control unit (304) configured to control the visual output of the display (318). The display (318) may use LCD (liquid crystal display) technology, LPD (light emitting polymer display) technology, and/or LED (light emitting diode) or OLED (organic LED) technology, although other display technologies can be used in other examples. As mentioned above, the display (318) may also use touch sensing technology, including but not limited to, capacitive, resistive, infrared and surface acoustic wave technologies, other proximity sensor arrays, or other elements for determining one or more points of contact with the display (318), such that the display (318) may also act as a touchscreen. The control unit (304) may include electronics capable of outputting visual signals to the display (318). In the variation depicted in FIGS. 3A and 3B, the memory unit (310) may be configured to store data relating to a plurality of visual outputs for the display (318) and the processor (306) may be configured to select a specific visual output from the plurality of visual outputs and communicate with the display (318) such that the selected specific visual output appears on the display (318). While the display (318) is depicted in FIGS. 3A and 3B as an integrated display, the analyte measurement device (300) may not comprise a display (318) and a separate interface may be used to display information (e.g., a cellular phone, computer, tablet, etc.).

In some embodiments, the analyte measurement device (300) may also be configured to detect and respond to audible commands. As depicted in FIG. 3B, the analyte measurement device (300) may comprise a microphone (312) configured to detect sound, and a control unit (304) configured to interpret and control how the detected sound is utilized by the analyte measurement device (300). The control unit (304) may include electronics capable of detecting sound and converting it into instructions for the device. For example, the control unit (304) may comprise a processor (306), a speech unit (308), and a memory unit (310). The microphone (312) may be configured to detect an audible command and convert it into a data signal, the speech unit (308) may be configured to convert the data signal into instructional data for the analyte measurement device, the memory unit (312) may be configured to store instructional data relating to a plurality of instructions, and the processor (306) may be configured to select a specific instruction from a plurality of instructions stored on the memory unit (312) and implement it. In some embodiments, the analyte measurement device (300) may include a headset jack instead of, or in addition to, a microphone (310). The headset jack may provide an interface between the speech unit (308) and removable audio input devices, such as an external microphone or a headset with both an output (e.g. a headphone for one or both ears) and an input (e.g., a microphone).

In some variations, the analyte measurement device may communicate with and provide auditory, visual, or other information to a separate user device. For example, FIG. 3B depicts a variation of an analyte measurement device (300) comprising RF (radio frequency) circuitry (316). The RF circuitry (316) may receive and send RF signals. The RF circuitry (316) may convert electrical signals to/from electromagnetic signals and communicate with communications networks and other communications devices via the electromagnetic signals. The RF circuitry (316) may comprise well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The RF circuitry (316) may communicate with networks, such as the network (406) illustrated in the exemplary communication system (400) depicted in FIG. 4.

Figure 4:
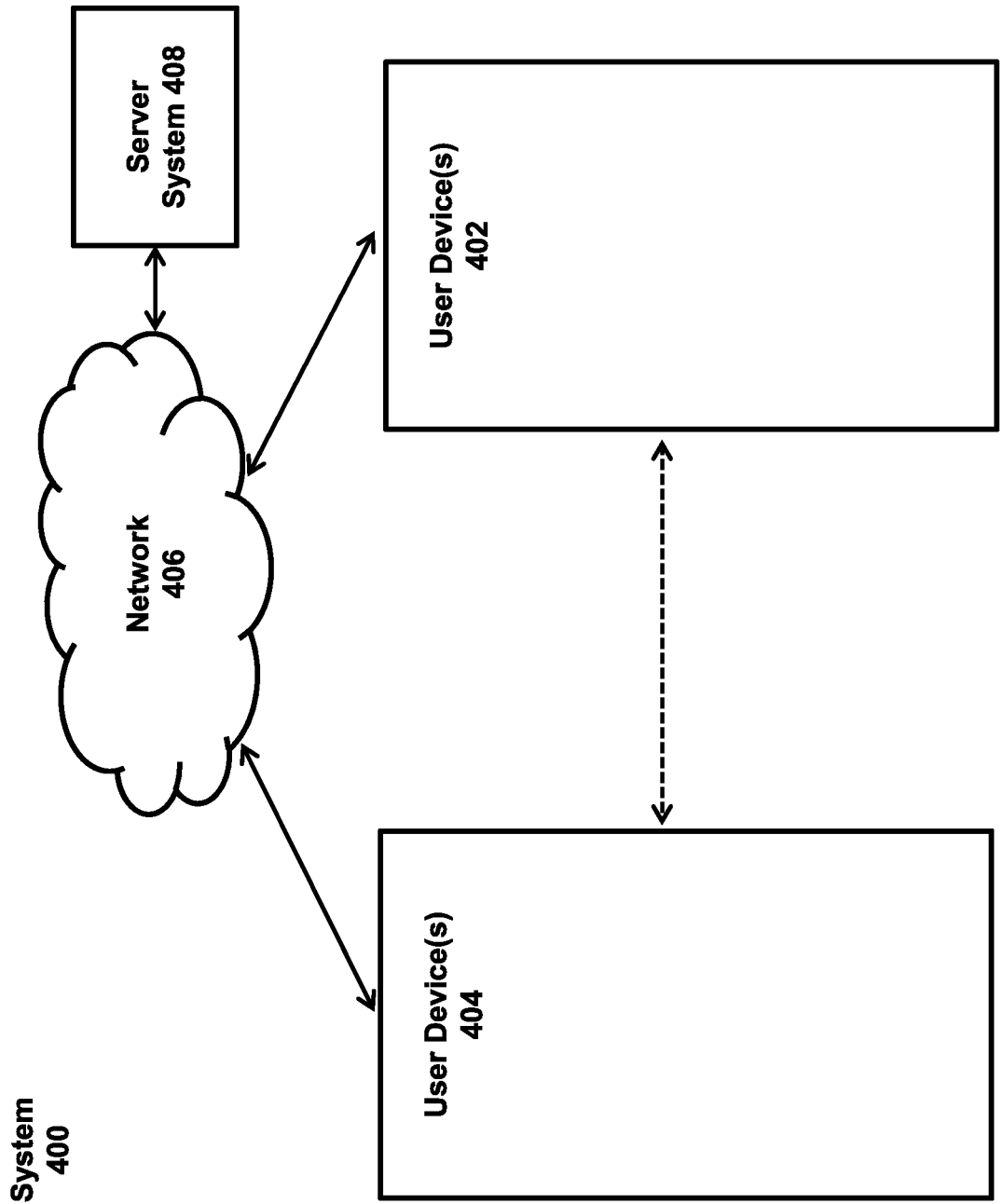
FIG. 4 depicts a schematic representation of a server system.

FIG. 4 depicts an exemplary system (400) for sending and receiving auditory, visual, or other information between user devices (402, 404). The first user device (402) may be an analyte measurement device, such as the analyte measurement device (300) depicted in FIGS. 3A-3B, and the second user device (404) may include any of a variety of devices, such as a cellular telephone (e.g., smartphone), tablet computer, laptop computer, desktop computer, portable media player, wearable digital device (e.g., digital glasses, wristband, wristwatch, brooch, armbands, etc.), television, set top box (e.g., cable box, video player, video streaming device, etc.), gaming system, or the like. While two user devices (402, 404) are depicted, any number of user devices (402, 404) could be included in the system (400).

The user devices (402, 404) may transmit data (e.g. user data, test data, audible prompts, visual prompts, etc.) to the server system (408) through the network (406). The network (406) may include any of a variety of networks, such as a cellular telephone network, WiFi network, wide area network, local area network, the Internet, or the like. The user devices (402, 404) may communicate with the network (406) by wireless communication. The wireless communication may use any of plurality of communication standards, protocols and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol. In some variations, the user devices (402, 404) may directly communicate with each other without transmitting data through the network (406) (e.g., through NFC, Bluetooth, WiFi, and the like.)

The server system (408) may include a server, storage devices (including cloud based storage), databases, and the like and can be used in conjunction with the user devices (402, 404) to transmit data. For example, in variations in which one of the user devices (402) is one of the analyte measurement devices (300) depicted in FIGS. 3A-3B, the user device (402) may receive information from a user, optionally process the information, transmit some or all of the entered and/or processed information to the server system (408), receive information from the server system (408), and output an auditory, visual, or tactile prompt from the device (402). The user device (402) may optionally transmit information to the second user device (404) which may also output an auditory, visual, or tactile prompt. In some embodiments, both user devices (402, 404) may receive information from the server system (408), and output an auditory, visual, or tactile prompt. In some variations, the server system (408) may process and/or store the information. In some instances, the user device (402) may receive and process information without the server system (408) and/or the network (406) and may transmit information about an auditory, visual, or tactile prompt to the server system (408) to transmit to the second user device (404), which may receive the information and output an auditory, visual, or tactile prompt. Any type of information can be transmitted and the server system (408) and the user devices (402, 404) may transmit information through the network (406) as many times as necessary.

For the purposes of this application, a specific output and any data or signal corresponding thereto will be referred to as a "prompt." Likewise, for the purposes of this application, a specific user input and any data or signal corresponding thereto will be referred to as a "command." For example, a specific sound output and any data or audio signals corresponding thereto will be referred to as an "auditory prompt," a specific visual output and any data corresponding thereto will be referred to as a "visual prompt," and a specific auditory input and any data or audio signals corresponding thereto will be referred to as an "auditory command."

An auditory prompt may include speech, music, sounds, combinations thereof, and the like, such as will be described in more detail below. In some instances, the analyte measurement device may be configured to produce auditory prompts that can audibly guide users through one or more operations of the device. For example, in variations where the analyte measurement device is an integrated device, the analyte measurement device may be configured to audibly guide a user through an entire sampling process to obtain and analyze a fluid sample to determine a concentration or other measurement of a target analyte. As an example, some variations of the analyte measurement devices described here may audibly inform a user that the device has been woken from a sleep/powered off state, that the device is ready to acquire a sample, that the device is acquiring a sample, that a sample has been acquired (or in some instances, that an additional sample needs to be applied to the device), and that the sample is being analyzed. The analyte measurement device may then present the results of the analysis (e.g., a concentration of blood glucose in the sample).

A visual prompt may include text, graphics, symbols, or combinations thereof, and the like, such as will be described in more detail below. Similarly to the audible prompts discussed above, in some instances the analyte measurement device may be configured to produce visual prompts that can visually guide a user through one or more operations of the device or otherwise convey information about a user's testing history or results.

An auditory command may include speech or sounds, or a combination thereof, and the like, such as will be described in more detail below. A user may use auditory commands to instruct the analyte measurement device to perform specified tasks.

Prompts

Typically, analyte monitors (such as glucose monitors) visually communicate information to a user (e.g., via a display). For example, the analyte monitors may visually display a concentration of an analyte in a sample (e.g., a glucose reading), or may visually display prompts that instruct the user to take one or more actions associated with an analyte measurement operation (e.g., insert a test strip or other test media, apply a sample to the test media, wait for analysis). This type of visual communication normally consists of simple text appearing on the display. The analyte measurement devices described here may be configured to provide information visually and/or audibly to a user (e.g., via the display (318) or the speaker (302) of the device (300) shown in FIG. 3A) in a customized manner. Generally, presenting information audibly may promote or otherwise facilitate the use of the analyte measurement devices by users with vision problems, as auditory prompts may allow a vision-impaired user to perform actions with the device (e.g., to complete the analysis of an analyte) without needing assistance from another user. Additionally, presenting information (visually, audibly, or otherwise) in a customized manner, as will be discussed in more detail below, may provide a more enjoyable user experience and may therefore increase user compliance (e.g., whether the user tests as directed).

Generally, the analyte measurement devices described here may be configured to output one or more prompts during use of the device. Typically, a prompt may be outputted in response to an action taken by a user or on a scheduled basis. For example, in some variations an analyte measurement device may provide a prompt when the device is powered on or otherwise awoken from a low-power sleep state. The prompt may provide a greeting, may inform a user of the current time, or the like. When a user initiates an analyte measurement operation (e.g., a testing sequence), the analyte measurement device may output one or more prompts that may guide the user through one or more steps of the analyte measurement operation. For example, a prompt may instruct a user to insert a test strip into the device, to place a sampling site such as a finger on a test port, to apply or reapply a sample to a test port, combinations thereof and the like. Prompts may also instruct a user as to the status of the analyte measurement operation (e.g., a prompt may inform a user that the device is obtaining a sample or is analyzing the sample) or the results of the analyte measurement operation (e.g., the concentration of a given analyte in the sample). The analyte measurement devices may also be configured to output multiple prompts at the same time. For example, the analyte measurement devices may be configured to output both an auditory prompt and a visual prompt in response to a single action taken by a user or on a scheduled basis.

Figure 5B:
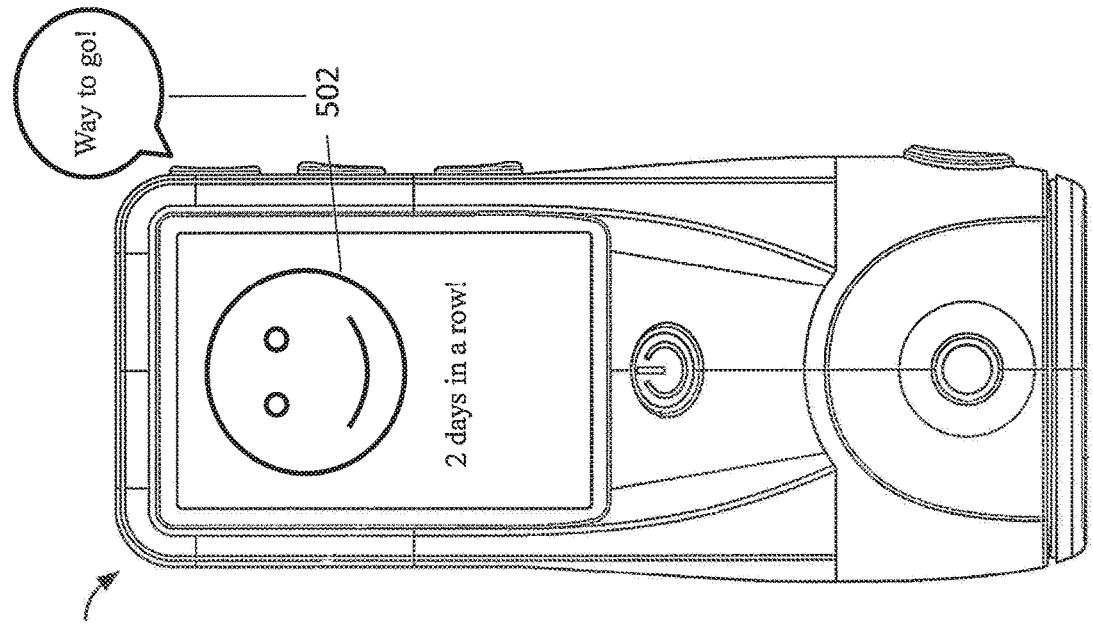
FIGS. 5A and 5B depict front views of a variation of the analyte measurement devices described here.
Figure 5A:
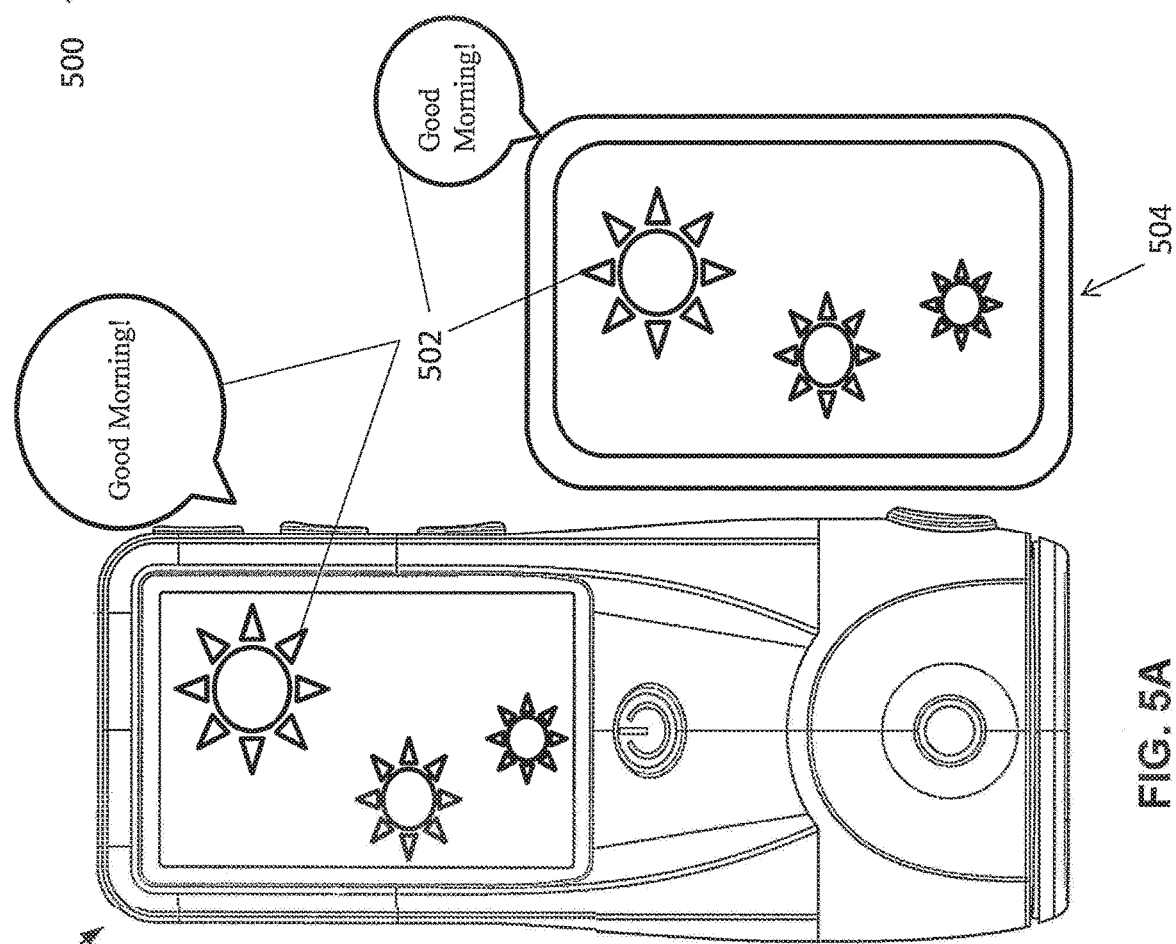

Turning to FIGS. 5A-5B, in some variations, one or more prompts (502) may be dependent on a specific time, date, measurement, or use of the device (500). The analyte measurement device (500) may be configured to receive, compile, store, and/or access data, as is described above in more detail. In some variations, the analyte measurement device (500) may incorporate this data in the given prompts (502). FIG. 5A depicts an example of a variation of the devices (500) described here outputting a prompt (502) that may be dependent on the time of day. As seen there, the device (500) may be configured to recognize the time of day (e.g., morning) and to output a prompt or prompts (502) that correlate with it (e.g., a rising sun, "good morning"). The device (500) may be configured to recognize any time of day (e.g., lunch time, evening, night, hours during which the user is at work, hours at which the user is sleeping, etc.) and may output prompts that correlate with the recognized time. In other variations, a device may output a prompt (502) on certain days of the week (e.g., "Happy Friday," graphic of calendar with day of week or date), or certain days of the year (e.g., "Happy birthday!", graphic of birthday cake, display age with balloons). In some instances, a prompt (502) may be dependent on the user's testing frequency. For example, as described above in more detail, the analyte measurement device (500) may be configured to record the number of analyte measurement operations performed by a user during a given span of time and the corresponding results, and create a data set that can later be referenced by the device. The analyte measurement device (500) may be configured to output a prompt (502) that provides the user with information about his/her testing history and results. For example, the analyte measurement device (500) may output a prompt (502) that informs a user of his/her compliance with an expected testing regimen (or lack thereof), that encourages the user to better comply with the regimen, that informs a user of how many tests he/she has completed (consecutively, this week, total, etc.), and the like.

For example, if a user is complying with the expected testing regimen (e.g., consecutively or consistently testing at prescribed times), the prompt (502) may praise the user (e.g., "You're doing great! Keep it up!", "Way to go! You've tested 4 days in a row!", a graphic of a medal with a numerical indication of compliance, graphic of a check mark, etc.). Conversely, if the user is not complying with the expected testing regiment, the prompt (502) may inform the user of this ("You haven't been testing 2 times a day as prescribed by Dr. Simmons. Maybe you should test more often", graphic of a sick patient, graphic of an "X", etc.).

Similarly, the prompts (502) may depend on the results of one or more analyte measurement operations, as is depicted in FIG. 5B. For example, if a concentration or the concentrations measured during the analyte measurement operations is consistently within a prescribed range (e.g., for three consecutive tests, two out of three consecutive tests, or the like), the prompt (502) may praise the user (e.g., "Your results look great", graphic of a smiley face, etc.). If a concentration or the concentrations measured is consistently outside of a prescribed range (e.g., for three consecutive tests, two out of three consecutive tests, or the like), the prompt (502) may encourage the user to test more frequently, to consult a physician or to change the user's diet (e.g., "You may want to test more often," "You may want to speak to Dr. Simmons about your test regimen", a graphic of a doctor on the telephone, a graphic of a piece of candy, etc.). If a user consistently tests at certain times throughout the day and the user fails to test at a time previously identified as a regular testing time, the prompt (502) may remind the user to test ("Did you forget to test today?", graphic of an analyte measurement device flashing on the display with a question mark, etc.). If the time a user tests is consistently outside of a prescribed or historically calculated range, the prompt (502) may remind the user to test before the prescribed or historically calculated range passes (e.g., "Don't forget to test at 2 pm", graphic of a set clock and an exclamation mark, etc.).

Moreover, one or more of the prompts (502) may depend on the results of a determination of when a glucose event may occur, as is discussed in detail above. For example, a prompt (502) may inform a user of the likelihood of a glucose event occurring (e.g., "80%", graphic of a partially filled thermometer with a scale from 1-100%, etc.). In some variations, the prompt (502) may inform a user that a glucose event may occur imminently (e.g., "You may begin to feel dizzy", a graphic of a hospital, etc.) and/or that immediate action is required (e.g., "Please test immediately", "Please eat carbohydrates", a graphic of a user testing, a graphic of a suggested food, etc.). In some variations, the prompt (502) may inform a user that a potentially glucose event may occur in the future (e.g., "You may have low blood sugar in 2 hours", "graphic of clock with an exclamation point, etc.) and/or suggest an action the user may wish to take in the future (e.g., "Please test again in 1 hour", "Please eat a snack in 30 minutes", a graphic of a clock with an analyte testing device, etc.).

While the prompts (502) are described as being output to/on the analyte measurement device (500) itself, in some variations, the prompts may be output on a separate device (504) in communication with the analyte measurement device, as is described above in detail with respect to FIG. 4. For example, a user may interact with an analyte measurement device (500) in some capacity (e.g., turn the device on, turn the device off, begin a test sequence, finish a test sequence, etc.) and a prompt (502) may be output on one or more separate devices (504) (e.g., a cellular phone, computer, tablet, etc.). In some variations, a prompt (502) may be output on a separate device (504) that is used or can be accessed by another person (e.g., a computer at the user's doctor's office, a cellular phone of a relative or caretaker, etc.). In other variations, a prompt (502) may be output on a separate device (504) that is used or can be accessed by the user (e.g., the user's cellular phone, the user's computer, the user's headphones (for audible prompts) etc.). In some embodiments, a prompt (502) may be output on both the analyte measurement device (500) and a separate device (504), as is depicted in FIG. 5A. Additionally, in some embodiments, the analyte measurement device (500) may be in communication with applications that are running on or are stored on a separate device (504), and may be able to receive and/or send data to/from the applications on the separate device (504). For example, in an embodiment in which a prompt (502) may be output to inform the user that a glucose event may occur now or in the future, the analyte measurement device (500) may communicate with an alarm clock application running or stored on a separate device (504) and may program the alarm clock to sound at a later time to output the prompt (502).

Commands

Generally, the analyte measurement devices described here may be configured to receive one or more commands during use of the device. Typically, a command may be given by a user and received by the device. For example, in some variations, a user may give a command after the device is powered on or otherwise awoken from a low-power sleep state. The command may provide instructions to the device or may otherwise communicate an action the user desires the device complete. For example, a user may provide an audible command (e.g., "Wake-up", "Turn-Off", "Begin Test", etc.), the device may receive the audible command, and the device may respond by completing the user's desired instruction (e.g., waking-up from low-power sleep state, turning-off, beginning a test sequence, etc.). In some variations, the user may provide an audible command requesting information about the user and/or his/her current or historical test results (e.g., "What is my blood sugar?", "What was my blood sugar on Tuesday?"), the device may receive the command, access the requested information, and respond with a prompt comprising the information requested by the user. In some embodiments, the requested information may comprise information about the status of the testing sequence or any other information that may be of interest to a user.

Auditory Prompts

As mentioned above, the analyte measurement device may output an auditory prompt in response to an action taken by the user (e.g. starting a test sequence) or on a scheduled basis (e.g. a reminder to test at a certain time every day). Auditory prompts may also be used to read on-screen menus and options, to guide a user through setting or changing one or more options (e.g., setting a device clock, setting an alarm or reminder, controlling a vacuum pump or display backlight). Table 1 below provides a plurality of examples of auditory prompts that may be outputted by the analyte measurement devices described here.

TABLE 1

| Auditory prompt | Possible Triggering Action | Examples |
|---|---|---|
| Auditory prompt configured to alert user that device is in an operational state and/or provide a greeting | Device is powered on/awoken from low-power sleep state | "Welcome to POGO ®" "Good morning, Jane" "The time is 3:21 pm" "The device is ready for use" |
| Auditory prompt to instruct user to position a sampling site (e.g., a finger) relative to a sample acquisition portion of the device (e.g., a test port) | User activates a analyte measurement operation | "Please apply your finger to the test port" |
| Auditory prompt to indicate that sampling or lancing will occur (e.g., the device will penetrate the skin and/or extract a sample) | The analyte measurement device determines that the sampling site is positioned relative to a sample acquisition portion | "Prepare for sampling: 3. 2. 1." |
| Auditory prompt to instruct user to maintain sampling site position and/or provide status of sampling | The analyte measurement device has pierced or lanced the sampling site | "POGO ® is obtaining a sample, please hold your finger on the test port." |
| Auditory prompt to alert a user that a usable sample has been acquired. | The analyte measurement device determines that a sample has been acquired | "Sample Acquired." |

TABLE 1-continued

| Auditory prompt | Possible Triggering Action | Examples |
| --- | --- | --- |
| Auditory prompt to alert a user to apply additional sample to the device (e.g., if the device determines that an insufficient volume of fluid has been captured by the device) | The analyte measurement device determines that a sufficient sample size has not yet been acquired | "Please apply additional sample." |
| Auditory prompt to alert a user that a result has been obtained and/or measured values | The analyte measurement device has completed an analyte measurement operation | "Your blood glucose is 126 mg/mmol." |

Visual Prompts

Also as mentioned above, the analyte measurement device may output a visual prompt in response to an action taken by the user (e.g. starting a test sequence) or on a scheduled basis (e.g. a reminder to test at a certain time every day). Visual prompts may also be used to guide a user through a test sequence (as is described above in Table 1 with respect to auditory prompts). Visual prompts that guide a user through a test sequence may comprise any visual representation of the steps of the test sequence. For example, simple text may appear on a display explaining what the user should do or a graphical representation of the steps may appear (e.g., a graphic of a finger applied to the test port when a user should apply his/her finger to the test port).

Other types of visual prompts are also contemplated. In some embodiments a light source (e.g., LED) may illuminate a component of the device. For example, a component (the display, a bezel of the display, the test port, the buttons, etc.) may flash or change colors. In some embodiments, the color the component is illuminated may vary based on a user's testing history. For example, if a user has not missed any tests in his/her expected testing regimen, the component may illuminate green. If a user has missed between 0 tests and a selected set-point (e.g. 3 tests, 4 tests, etc.), the component may illuminate yellow. If a user has missed more than a selected set-point of tests, the component may illuminate red. Illumination of the component may be tied to any of a number of variables (e.g., missed tests as described above, time since last test, etc.), and any appropriate set-point (e.g., 3 tests, 3 days since last test, etc.). The set-point may be pre-programmed into the device, input by the user, input by a doctor, or received by the device from an external source. The component may also begin to flash or pulse based on a user's testing history or it may both be illuminated a specified color and flash or pulse.

In some embodiments, visual prompts may be utilized to convey data about a user's testing patterns, trends, and/or results. For example, in some instances, a visual prompt may comprise a graphic that may move or otherwise change positions based on a specified variable (e.g., time, testing frequency, testing consistency, amount of sample received, status of analyte measuring operation, etc.). For example, a graphic may be displaced along the x-axis, the y-axis, or both the x and y axes consecutively or concurrently to convey a change in a specified variable. In some embodiments, a graphic may rotate to indicate a change in a specified variable, or its size or depicted volume may increase or decrease. In other embodiments, a graphic's movement may comprise a combination of displacement, rotation, and volumetric changes.

Figure 6B:
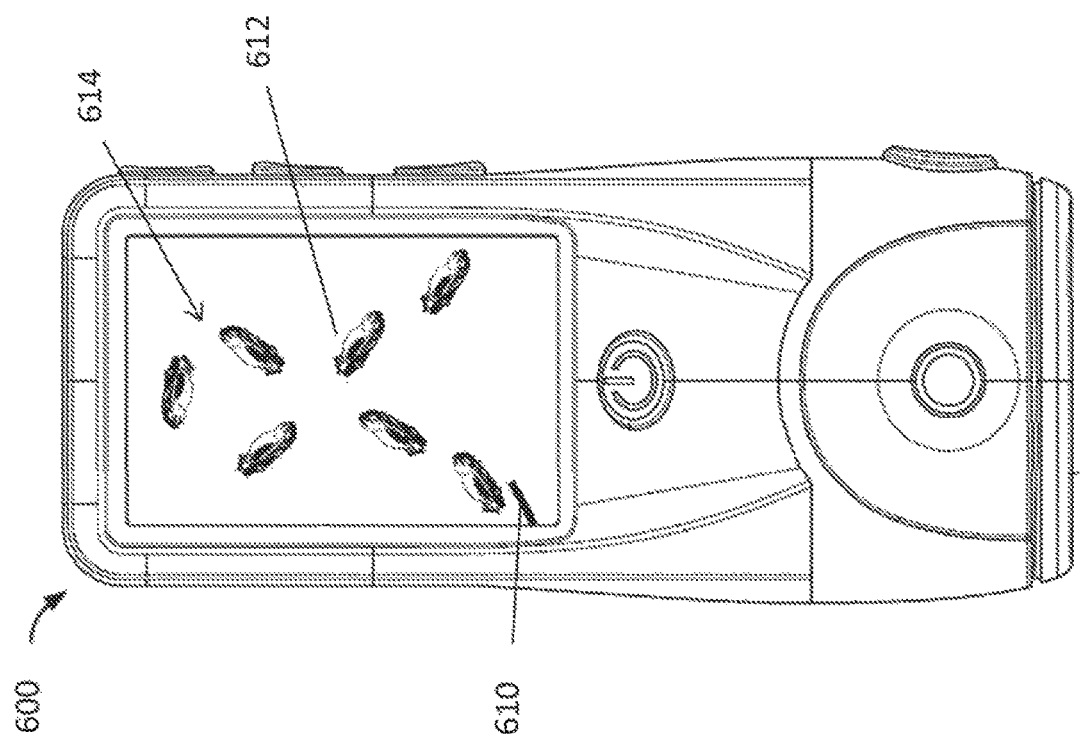
FIGS. 6A and 6B depict front views of a variation of the analyte measurement devices described here.
Figure 6A:
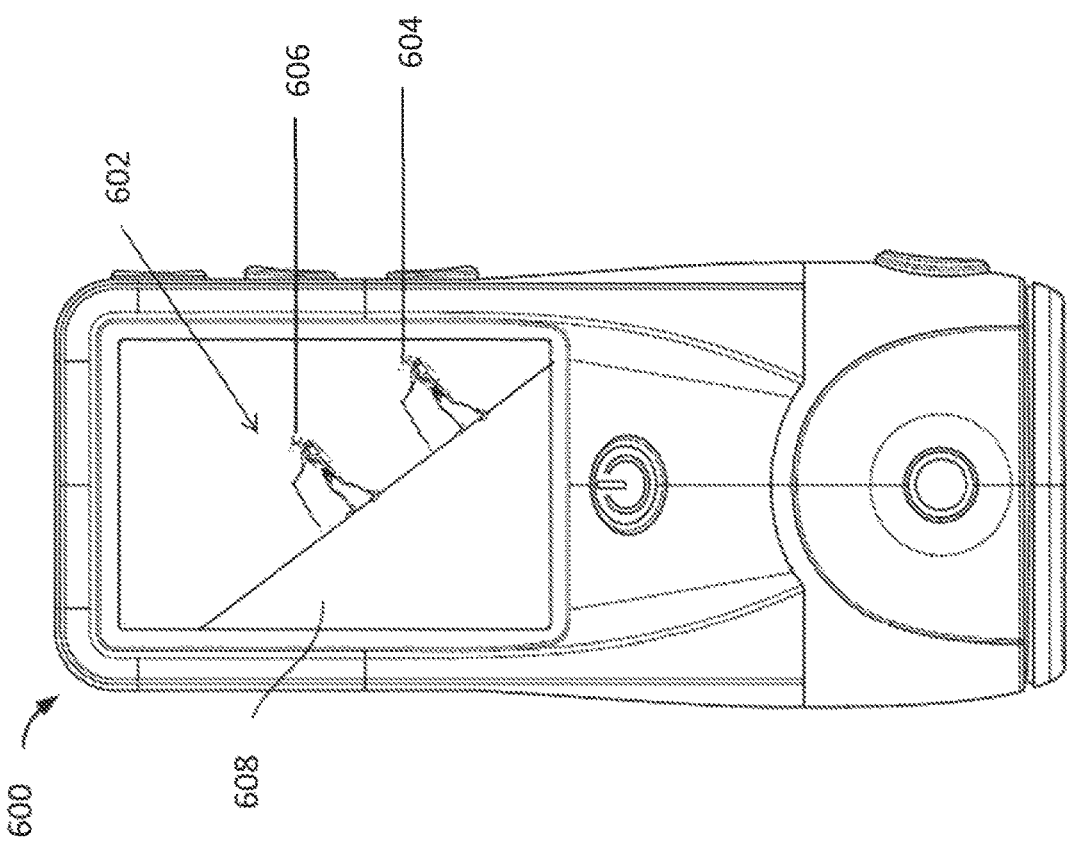

In some variations, the graphic may change based on the cumulative results of many tests (e.g., number of tests completed in a specific time frame, number of tests with results within a desired range, number of tests completed consecutively, number of days with completed tests within desired range, etc.). For example, each time a user finishes a test, the graphic may be modified to reflect the cumulative result of all of the completed tests. In some instances, the graphic may be modified such that it moves from a first pre-test position to a second post-test position. The movement of the graphic from the first pre-test position to the second post-test position may convey information to the user about the user's testing patterns or results. For example, FIG. 6A is an illustrative example of an analyte measurement device (600) outputting such a visual prompt (602). The visual prompt (602) comprises a mountain (608) with a hiker depicted in a first position (604) and a second position (606). In this example, the mountain (608) may be a graphical representation of the number of tests a user must complete during a set time frame (e.g. 1 day, 2 weeks, etc.) to be fully compliant with the user's regimen. The hiker in the first position (604) may graphically indicate how many tests the user has completed thus far during the set time frame and may appear before a user begins a test sequence. After the user completes the test sequence, the hiker in the second position (606) may appear to indicate to the user that he/she is closer to completing all of the tests necessary to be compliant during the set time frame. In some embodiments, the hiker's displacement from the first position to the second position may appear on the screen such that the hiker appears to be moving. Additionally, it should be appreciated that while the hiker is moving in both the x-axis and the y-axis, the graphics may be configured to move in any direction or to rotate. The graphics may also be configured to move along a rotational path. In some embodiments, the graphic may only move horizontally and vertically and may not rotate, while in other embodiments the graphics may rotate and move in any direction (e.g. along a linear path, rotational path, a zig-zag path, etc.).

In some instances, the graphic may change based on data collected during a single test (e.g., time since test sequence began, number of steps of test sequence completed/remaining, amount of sample collected, etc.). For example, the device may output an active visual prompt as the graphic may change in real-time while the analyte measurement device is completing an analyte measurement operation. As an example, the active visual prompt may comprise a cat drinking water from a bowl and expanding in volume while the device collects a sample from a user. The cat's volume may be indicative of the amount of sample the device has collected and the cat may finish drinking water and move away from the bowl when the device collects a sufficient sample volume. Another example of an active visual prompt (614) is depicted in FIG. 6B. The visual prompt (614) may comprise a graphic that moves along a specified trajectory as an analyte measurement operation is occurring. Specifically, the graphic may be at the beginning of its specified trajectory or path when the user begins the analyte measurement operation, it may be displaced such that it is at the midpoint of its specified trajectory when the analyte measurement operation is half-way completed, and it may be displaced such that it is at the end of its specified trajectory when the analyte measurement operation is complete. For example, FIG. 6B depicts a racecar (612) exiting a ramp (610) and completing a rotation in the air. In this example, the racecar (612) may appear on the device (600) when a user begins a testing sequence. The racecar (612) may move vertically and horizontally along a specified trajectory while the testing sequence is taking place such that the racecar's (612) movement tracks the progress of the testing sequence. For example, the racecar (612) may begin exiting the ramp (610) when the user begins the test sequence, the racecar (612) may have rotated 180 degrees when the user is half-way through the test sequence, and the racecar (612) may appear to be landing when the test sequence is complete. The above embodiments are merely examples and any suitable graphical representation could be used.

Customization

As discussed above, the analyte sampling devices may be configured to output a plurality of different prompts. In some variations, the specific prompts outputted by the analyte measurement devices may be customized in one or more ways. Generally, the analyte measurement device is programmed with a plurality of "prompt types." Each prompt type indicates an instance during which the analyte measurement device may output a prompt. For example, an analyte measurement device may be configured with a first prompt type (e.g., providing a prompt when the device is powered on or awoken from a low-power sleep state), a second prompt type (e.g., providing a prompt when a user has performed a given number of consecutive tests in a given time frame), and a third prompt type (e.g., providing a prompt when the device has completed an analyte measurement operation). For each prompt type, the analyte measurement device may be programmed with one or more prompts that may be selected for that prompt type. The analyte measurement device may be figured to select a prompt for each prompt type, and these selections are collectively referred to as a prompt set. It may be possible for a user or the device to select from one of a plurality of possible prompt sets, and the currently selected prompt set is referred to here as the active prompt set. The active prompt set may be manually set by a user, or may be automatically determined by the analyte measurement device, as will be discussed in more detail below. While typically a single prompt is selected for each prompt type of a prompt set, in some instances a plurality of different prompts may be selected for a given prompt type in a prompt set. In these instances, when the analyte measurement device determines that conditions for outputting the prompt type have been met, the device may select one of the plurality of different prompts in a random or predetermined order. Additionally, for the purposes of this application, when a specific prompt of a prompt type is intended to convey a measurement or time (e.g., a concentration of an analyte in a sample, the duration of time that has passed between measurements, the number of consecutive days the device has performed a testing operation, the current time, etc.), the prompt is considered a single prompt even though the actual measurement or time conveyed by the prompt may vary depending between instances that the prompt is output.

When two or more prompts are used for a given prompt type, the prompts may vary in any suitable manner. In some variations, a prompt type may have auditory prompt variations where different language is used (e.g., "Welcome to POGO®" in a first variation, "Let's test your glucose!" in a second variation). In other variations, a prompt type may have visual prompt variations where different graphics are used (e.g., a sun-rising in a first variation, a bowl of cereal in a second variation). In some embodiments, a prompt type may have an auditory prompt, a visual prompt and a tactile prompt associated with it. In embodiments in which multiple prompts (e.g., visual, auditory, tactile) are associated with a prompt type, and the prompt type comprises prompt variations (e.g., 2 different visual prompts, 2 different auditory prompts), any combination of the prompts may be used and the combinations may be selected in any suitable manner (e.g. by the user, at random, etc.).

Specifically with respect to auditory prompts, a prompt may have variations where different voices are used (e.g., a female voice in a first variation and a male voice in a second variation). Additionally or alternatively, a prompt may have variations where different sound effects are associated with a prompt (e.g., when a prompt gives positive reinforcement for frequent testing, such as "Way to go! You've tested 4 days in a row," a first variation may include the sounds of a cheering crowd while a second variation may include a fanfare of trumpets).

In some variations, the device may be configured to allow a user to record one or more auditory prompts. For example, when an analyte measurement device will be used by a child, it may be desirable for the device to output auditory prompts that have been recorded by a parent or caretaker of the child. Providing auditory prompts with a familiar voice may provide an added level of comfort to the child as he or she uses the device, which may reduce fear associated with the device and may encourage the child to test more frequently. The recorded auditory prompts may be provided to the analyte measurement device in any suitable manner. In some variations, the auditory prompts may be recorded by the user on an external device (e.g., a computer, phone, tablet, recorder, or the like), and may be transmitted to the analyte measurement device (e.g., using a physical connection such as a USB connection and/or a wireless connection such as WiFi or RFID, as discussed in more detail above). In these variations, the external device may comprise a program that has a prompt recording mode configured to facilitate recording of specific auditory prompts, as will be discussed in more detail below.

In other variations, the analyte measurement device may be configured to record one or more auditory prompts. In these variations, the analyte measurement device may comprise a microphone or other sound recording device configured to capture a user's voice. Additionally, the analyte measurement device may be programmed with a prompt recording mode. When the device is placed in the prompt recording mode, the device may be configured to guide the user through recording one or more voice prompts. The prompt recording mode may be initiated during initial setup of the analyte measurement device, or may be selectively initiated by a user (e.g., through a menu command). The analyte measurement device may be configured to automatically guide the user through recording a predetermined number of auditory prompts (such as, for example, a given prompt set), or the user may select which auditory prompts he or she would like to record. For each auditory prompt that will be recorded in the prompt recording mode, the analyte measurement device may be configured to identify what prompt or prompt type will be recorded (e.g., "Please say a few words of encouragement", "Please repeat the following when instructed: 'Good morning!'"), instruct the user when to start and/or stop recording (e.g., "Please begin recording after the countdown, and press the power button when you have finished. 3, 2, 1."). When the auditory prompt has been recorded, the prompt recording mode may be configured to associate the recorded prompt with one or more prompt types (and in some instances, one or more prompt sets).

In some variations where an analyte measurement device may be used by multiple users, the device may be configured to select a different active prompt set for different users of the device. For example, one or more prompt types may include one or more prompts that are customized to a specific user. For example, when a prompt type is configured to provide an analyte measurement value, an active prompt set for a first user may output a first variation of an auditory prompt (e.g., "John, your blood glucose is 85 mg/mmol") or a visual prompt (e.g., a cheering man), while an active prompt set for a second user may output a second variation of an auditory prompt (e.g., "Sally, your blood glucose is 85 mg/mmol") or a visual prompt (e.g., a cheering woman). In some variations, prompts may be tailored to a given user, and may use information about that user (e.g., by using the user's name, the name of the user's physician, etc.). Additionally or alternatively, the prompts may be selected by the user based on his/her preferences (e.g., some users may prefer a male voice while other users may prefer a female voice). In some variations, prompts may be tailored to a given user using information from a user profile setup by the user, as was discussed above.

Generally, the analyte measurement device may be configured to store a user-specific prompt set for a plurality of individual users. When the device determines that one of the plurality of individual users is using the device, the device may be configured to automatically set the user-specific prompt set associated with that user as the active prompt set. In some variations, the analyte measurement device may be configured to select or load a specific prompt set based on information stored in a user's user profile. If the device is being used by an unrecognized user, the device may be configured to set a default prompt set as the active prompt set. Individual users may change their user-specific prompt set (e.g., using menu features or changing it in their user profiles), and new users may be added to the plurality of individual users. The analyte measurement device may be configured to differentiate between users in any suitable manner. In some variations, users may log into or otherwise input an identification code to the analyte measurement device to access or indicate to the device to access their user profiles. In some of these variations, a user may be required to log-in before the device may be used in an analyte measurement operation. Additionally or alternatively, a user may insert a USB stick, memory card, or the like into the analyte measurement device and the device may determine the user's identity from this component. Additionally or alternatively, a user may carry a key fob or other external device that may be wirelessly detected by the analyte measurement device to determine the user.

Removable or Additional Components

In some variations, the analyte measurement device may select an active prompt set (or a default active prompt set) based on one or more components of the device. In some instances, an analyte measurement device may be constructed and/or manufactured such the analyte measurement device may have one of a plurality of different physical appearances. For example, when the analyte measurement device comprises an outer housing (such as the meter housing (118) of the meter (100) discussed above with respect to FIG. 1B), the outer housing may be altered to change the physical appearance of the analyte measurement device. For example, the surface contours and/or the colors of the outer housing may alter the physical appearance of the analyte measurement device. Similarly, an outer housing may be configured with one or more visual patterns (e.g., chevron pattern, polka dots, etc.) and/or images (e.g., an animal, a race car, or the like).

Accordingly, in some variations, an analyte measurement device may be constructed and/or manufactured in one of a plurality of different configurations, in which each configuration has a different physical appearance. In some of these variations, each configuration of the analyte measurement device may have a default active prompt set associated with that configuration. Accordingly, systems and kits may include a plurality of analyte measurement devices having different physical appearances, each having an appearance-specific default active prompt set. In some instances, the default active prompt set for a given configuration of the device may be thematically associated with the physical appearance of the analyte measurement device. For example, one or more portions of the housing of one configuration of an analyte measurement device may include an image of a car, and the associated auditory prompt set may include car-related sound effects (e.g., revving engines, squealing tires) and/or speech (e.g., "Start your engines") and/or the associated visual prompt set may include car-related visual effects (e.g. driver in car turning key, rotating tires). Another configuration may include an image of a cat, and the associated auditory prompt set may include cat-related sound effects (e.g., purring, meowing) and/or speech (e.g., "That test was purr-fect") and/or the associated visual prompt set may include cat-related visual effects (e.g., person petting cat, cat appearing to speak). The analyte measurement devices may have any suitable number of different configurations, each having a graphic appearance and an associated set of prompts.

In some variations, a user may replace one or more components of the analyte measurement device and/or add one or more additional components to alter the physical appearance of the device. In some variations, the analyte measurement device may be configured to change the active prompt set in response to the replacement or addition of one of these components. In some instances, a portion of a housing of the analyte measurement device may be releasably attached to the analyte measurement device such that the releasable portion may be replaced with another variation of the releasable portion. In other variations, the housing may be configured to accept an additional component using snap fit connectors, sliding connectors, clips, or the like. Systems or kits may include a single removable housing portion or they may include a plurality of removable housing portions. In systems or kits that include a plurality of removable housing portions, the analyte measurement device may be configured such that one of the plurality of removable housing portions may be connected to the analyte measurement device at a time. The plurality of removable housing portions may have different physical appearances, such as described above, such that changing the removable housing portion of the analyte measurement device may change the appearance of the analyte measurement device. In some variations, changing the removable housing portion of the device may not significantly change the physical appearance of the device, but may still change the active prompt set. In some instances, the removable or additional housing portion may allow for the delivery of data to the device, for example, updated software or firmware.

Figure 7A:
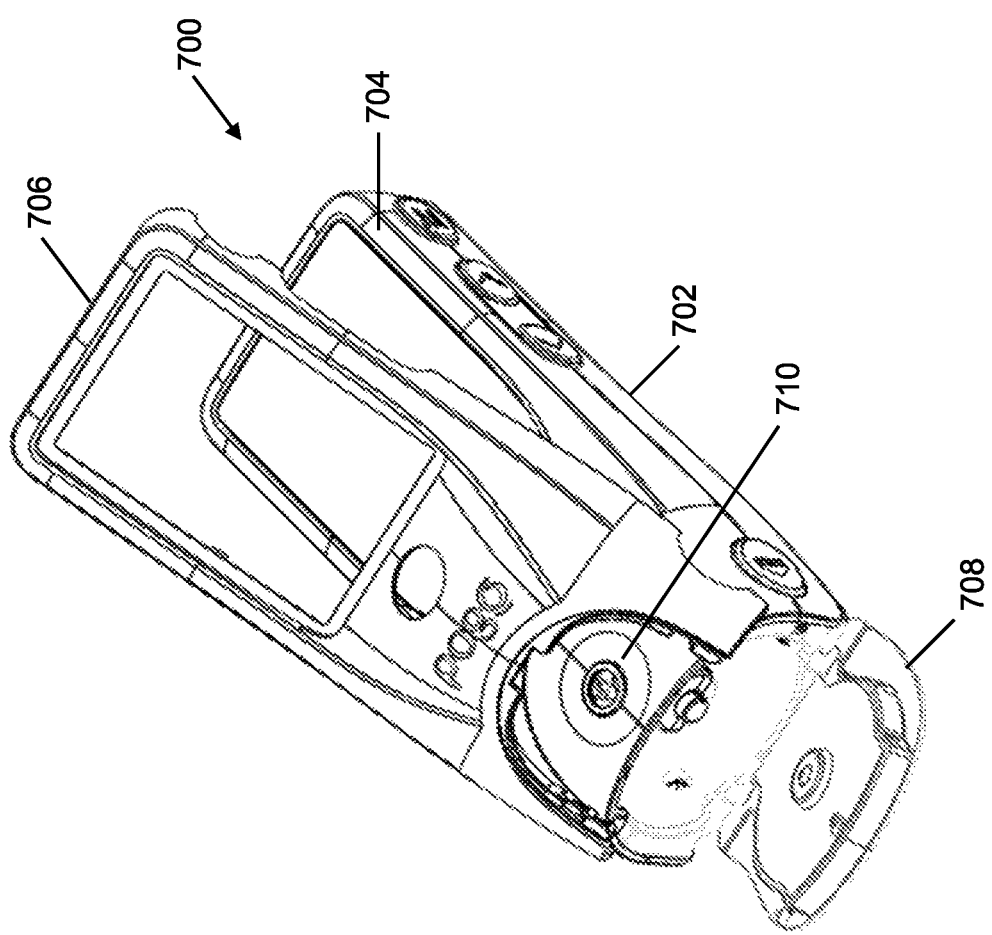
FIG. 7A depicts a perspective view of a variation of an analyte measurement device described here comprising an additional housing portion.
Figure 7C:
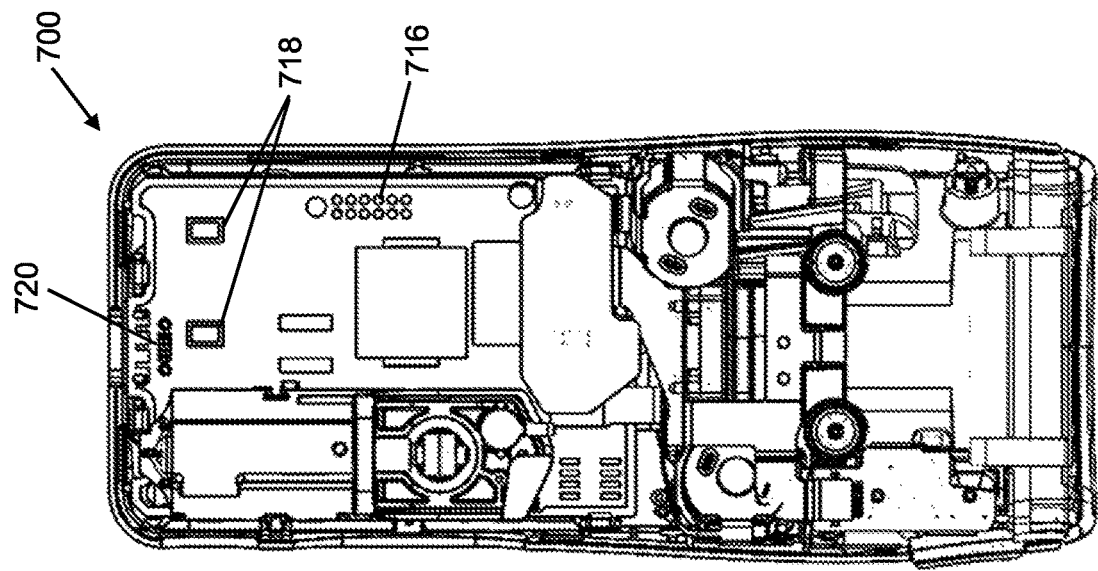
FIG. 7C depicts a back view of an analyte measurement device with the back cover removed.
Figure 7B:
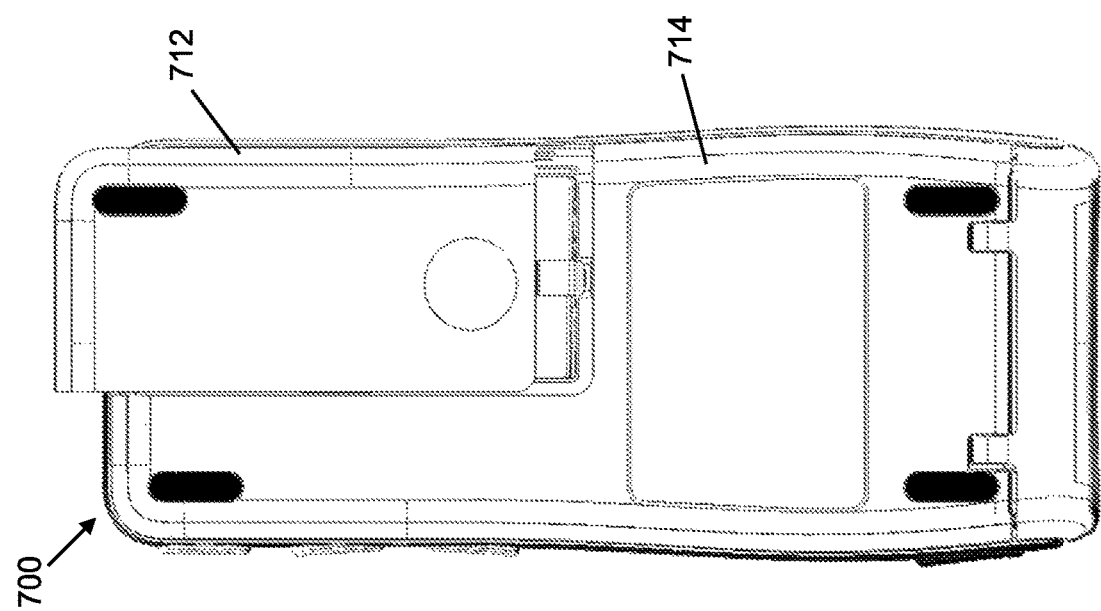
FIG. 7B depicts a back view of a variation of an analyte measurement device comprising a removable housing portion.

In some embodiments, the removable portion of the housing may be a front cover of the housing. For example, in the variation of the device shown in FIG. 1B, the meter housing (118) may comprise a removable front cover (132). In other variations, a front cover may be added to the housing. For example, in the variation of the analyte measurement device (700) shown in FIG. 7A, the housing (702) may comprise a first front cover (704) and may be configured to accept a second front cover (706). The second front cover (706) may alter the physical appearance of the device, change the active prompt set and/or deliver data stored within it to the device. In other embodiments, the removable portion of the housing may be a component other than the front cover. For example, as shown in FIGS. 7A and 7B, the removable portion of the housing may comprise the bottom (708), the port (710), the battery cover (712), the back cover (714), and the like.

In some embodiments, the cartridge may be configured to carry information relating to a prompt set. The cartridge (102) may comprise an information storage member (134) that carries information and may communicate with the meter (100) to convey the stored information. For example, the storage information member (134) may comprise one or more barcodes, as depicted in FIG. 1C. In these variations, the meter (100) may comprise one or more barcode scanners/readers. In variations where the cartridges are cylindrical or have an otherwise rounded cross-sectional area, the cartridge may be rotated to facilitate the reading of the barcode. In other instances, the meter (100) may be configured to move the cartridge into a position where the barcode may be read.

The cartridge may comprise any suitable number of barcodes (e.g., zero, one, two, three, or four or more barcodes). In some variations, the information storage member (134) may comprise one or more memory chips or cards, which may convey information to the meter through, for example, RF transmission, optical communication, or via direct electrical communication. In other variations, a separate memory card or chip may be packaged and/or provided with the cartridge. This memory card or chip may be inserted into a portion of the meter to convey information to the meter, as is discussed in more detail below.

As mentioned above, the analyte measurement device may be configured to change the active prompt set based on the removable portion that is currently connected to the analyte measurement device. In some variations, the analyte measurement device may be configured to automatically detect which removable portion is connected to the device and select an active prompt set associated with that removable portion. In some embodiments, the removable portion may comprise an identifier that may contain or transmit information or otherwise communicate with the analyte measurement device about the removable component connected to it and/or the prompt set (e.g., auditory, visual, etc.) associated with the connected removable component. For example, a system may comprise an analyte measurement device configured to receive a removable housing portion, and may further comprise a first version of the removable housing portion and a second version of the removable housing portion. The first version of the removable housing portion may have a first prompt set associated therewith, and the second version of the removable housing portion may have a second prompt set associated therewith. When the first version of the removable housing portion is attached to the analyte monitor, the analyte measurement device may be configured to detect the first version's identifier and set the first prompt set as the active prompt set. A user may remove the first version of the removable housing portion and connect the second version of the removable housing portion to the analyte measurement device. Upon connection of the second version of the removable housing portion, the analyte measurement device may detect the second version's identifier and may set the second prompt set as the active prompt set. In some variations, the identifier may be integrally formed with the prompt set.

Systems and kits may include a single removable housing portion or a plurality of versions of a given removable housing portion. Each version of the plurality of versions may have an associated identifier and prompt set, and the analyte measurement device may be configured to detect the version of the removable housing portion and set the associated prompt set as the active prompt set. In some variations, each version of the removable housing portion may include a different prompt set. A first prompt set may be considered different from a second prompt set if at least one prompt within the prompt set is different or if the prompt sets comprise different numbers of prompts.

Additionally or alternatively, as depicted in FIGS. 8A-8B, a skin (802) (e.g. a silicone case or the like) may be placed over and connected to a portion of the housing (804) of an analyte measurement device (800), which may change the physical appearance of the analyte measurement device (800). In these variations, the analyte measurement device (800) may be configured to detect the presence of an identifier in/on the skin (802), and may be configured to set a prompt set (auditory, visual, etc.) associated with the skin (802) as the active prompt set. In some instances, a system or kit may comprise a skin (802) comprising an identifier that is associated with a prompt set. In other variations, a system or kit may comprise multiple versions of a skin (802) (e.g., having different physical appearances or configurations), wherein each version comprises an identifier with a prompt set associated therewith. In these variations, the analyte measurement device may be configured to detect which version of the skin (802) is connected to the device (800) using the identifier, and may set the prompt set associated with that identifier as the active prompt set. For example, a system may include an analyte measurement device, a first version of a skin having a first prompt set associated therewith, and a second version of the skin having a second prompt set associated therewith. The skins may have different physical appearances, such as discussed above. In these variations, when the first skin is attached to the analyte measurement device, the analyte measurement device may be configured to detect the first skin's identifier and set the first prompt set as the active prompt set. A user may remove the first version and connect the second version of the skin to the analyte measurement device. In these instances, the analyte measurement device may be configured to detect the second skin's identifier and may set the second prompt set as the active prompt set. In some variations, the identifier may be integrally formed with the prompt set.

In variations where an analyte measurement device is configured to receive both a removable portion of a housing and a skin, the analyte measurement device may be configured to select the set of auditory prompts based on either the version of the removable portion or the version of the skin. In some of these variations, the presence of a skin may override the presence of the removable portion, such that the analyte measurement device is configured to set a prompt set associated with the skin as the active prompt set instead of a prompt set associated with the removable portion when both the skin and the removable portion are present. In some instances a user may be able to change the active prompt set even when a specific version of a skin or removable housing portion is attached to an analyte measurement device, by for example, changing a selection in a menu on the device.

The analyte measurement device may be configured to detect the identifier of a removable housing portion and/or a skin in any suitable manner. In some variations, a removable housing portion/skin may be configured to achieve direct electrical communication with a control unit of the analyte measurement device when attached to the analyte measurement device. For example, the removable housing portion or skin may include an electrical interface (such as a USB interface) that may physically contact an electrical interface of the analyte measurement device, and the analyte measurement device may be able to recognize or determine the presence and/or identifier of the removable housing portion/skin based on this electrical connection. Additionally or alternatively, one or more portions of the removable housing portion/skin may physically press against one or more buttons of the analyte measurement device to indicate the presence and/or identifier of a removable housing portion/skin. Additionally or alternatively, the removable housing portion/skin may be configured to wirelessly communicate with the analyte measurement device (e.g., via WiFi or RFID) such that the analyte measurement device may be configured to recognize or determine the presence and/or identifier of a removable housing portion/skin.

When the analyte measurement device is configured to set an active prompt set based on a prompt set corresponding to a removable housing portion's or skin's identifier, the specific prompts from the prompt set may be retrieved from any suitable location. In some variations, the analyte measurement device may be pre-programmed with the necessary prompts included in the various prompt sets. For example, if a system includes an analyte measurement device and a plurality of versions of a removable housing portion, each version having a corresponding prompt set, the analyte measurement device may be pre-programmed with the auditory prompts of each of the corresponding prompts. Additionally or alternatively, the analyte measurement device may be configured to retrieve one or more prompts from the removable housing portion/skin. In these variations, the removable housing portion/skin may be configured to store one or more prompts or prompt sets (e.g., in a memory such as flash memory or an integrated circuit), and the analyte measurement device may be configured to retrieve the prompts or prompt sets from the removable housing portion/skin. In some of these variations, the analyte measurement device may be configured to retrieve and use the prompts from the removable housing portion/skin without permanently storing the prompts in memory of the analyte measurement device. In other variations, the analyte measurement device may be configured to download and store the prompts from the removable portion/skin. In these variations, the downloaded prompts may be later selected (e.g., by a user) for use even when the specific version of the removable housing portion/skin has been removed from the analyte measurement device, using, for example, a selection menu. In still other variations, prompts or prompt sets associated with versions of a removable housing portion/skin may be downloaded from an external device (e.g., a computer, tablet, phone in communication with the analyte measurement device, a memory stick that may be inserted into the analyte measurement device, etc.) either via direct connection (such as a USB interface) or wireless connection (e.g., WiFi, RFID). In some variations, the removable housing portion/skin may contain updated software/firmware that may be transferred to the device when the removable housing portion/skin communicates with the device. The software/firmware updates may be contained on the removable housing portion/skin in addition to, or instead of, the prompt sets.

As mentioned above, the analyte measurement device may comprise a variety of components that enable the transfer of information from a removable housing portion/skin to the control unit of the device. FIG. 7C depicts a variation of the analyte measurement devices described here with the back cover (714) removed. In this embodiment, the analyte measurement device (700) may comprise electrical contacts (716) located below the batteries when the device is in use. The electrical contacts (716) may be configured to mate or otherwise communicate with corresponding electrical contacts on a removable housing portion, for example, a battery cover (712). Alternatively or additionally, the device (800) may comprise one or more wireless chips (718) that may communicate with one or more corresponding wireless chips contained in or on a removable portion of the device. In some embodiments, the device (800) may also comprise a USB port (720) that may physically contact a USB plug on the removable portion of the device. These components may mate with any removable or additional portion of the housing or with a skin, as described above.

Figure 8D:
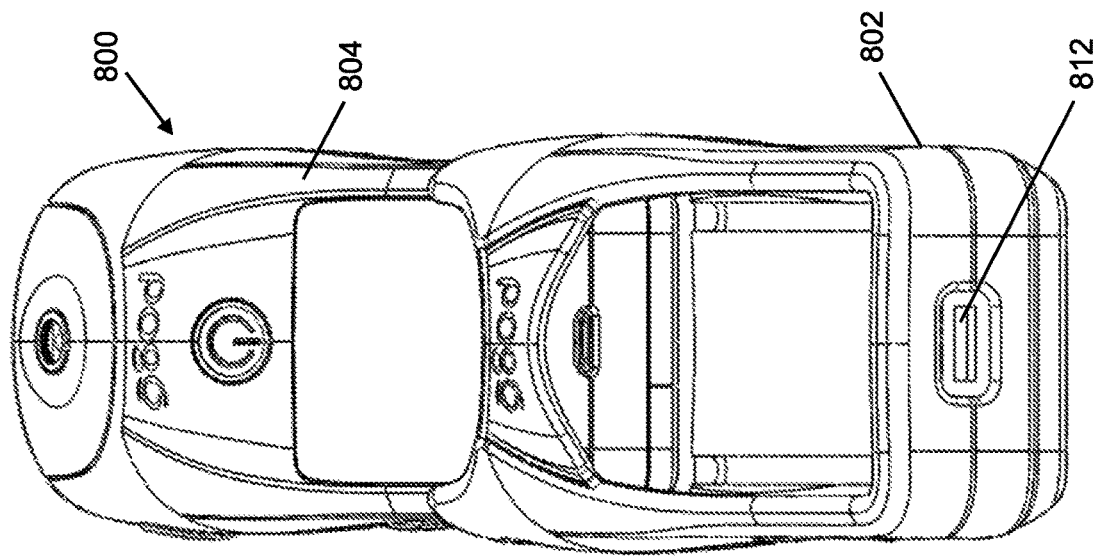
FIGS. 8C and 8D depict top perspective views of a variation of the analyte measurement devices described here without a skin, and with a skin, respectively.
Figure 8C:
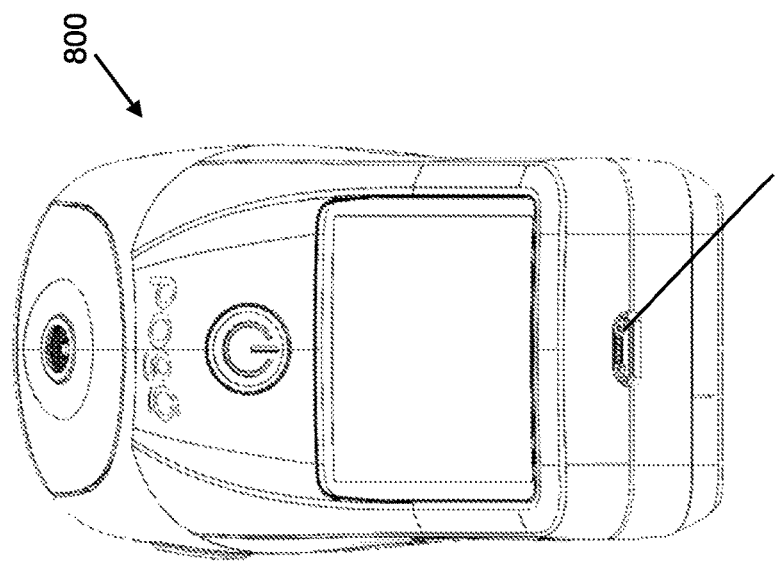

FIGS. 8A-8D illustrate another variation of the analyte measurement devices described here. FIGS. 8A and 8B depict front and perspective views of an analyte measurement device (800) with a skin (802) partially covering the housing (804). FIGS. 8C-8D depict a top perspective view of an analyte measurement device (800) without a skin (802), and with a skin partially covering the housing (804), respectively. The analyte measurement device (800) shown here may receive information from the replacement or addition of a skin (802). The skin (802) may comprise any suitable means for storing and transferring information. For example, the skin (802) may comprise a chip (806) that may store information and transfer it to the control unit of the device (800). In some variations, the skin may comprise a USB plug (808) that may physically contact a USB port (810) on the device (800). While the USB port (810) is depicted on the top of the device (800), it may be placed at any location that is suitable for connection to a skin (802) or other removable or additional housing portion. In some variations, the skin (802) may comprise both a USB plug (808) and a USB port (812) such that attachment of the skin (802) to the device (800) does not prevent the device (800) from connecting via USB to another component.

We claim:

1. A system comprising:
an analyte quantification member configured to react with an analyte in a fluid sample to produce a measureable response; and
an analyte measurement device configured to detect the measureable response and determine a concentration of the analyte, wherein the analyte measurement device comprises:
a housing comprising a releasable housing portion, wherein the releasable housing portion comprises an information transmitter that is associated with an auditory prompt set;
a speaker disposed within the housing; and
a control unit disposed within the housing, wherein the control unit comprises:
a non-transitory memory comprising instructions to detect the information transmitter, set the auditory prompt set associated with the detected information transmitter as an active prompt set, and output the active prompt set via the speaker, wherein the auditory prompt set associated with the releasable housing portion comprises an auditory prompt that warns a user of an impending lance with a skin penetration member by indicating an expiring time period until the lance occurs, and an auditory prompt that alerts a user that the analyte measurement device has acquired a usable sample; and a processor programmed to carry out the instructions on the non-transitory memory.

2. The system of claim 1 wherein the system further comprises a plurality of releasable housing portions.

3. The system of claim 2 wherein each of the releasable housing portions is associated with an auditory prompt set comprising at least one auditory prompt that differs from at least one auditory prompt associated with the other releasable housing portions of the plurality of releasable housing portions.

4. The system of claim 1 wherein the auditory prompt set associated with the releasable housing portion is stored on the non-transitory memory.

5. The system of claim 1 wherein the releasable housing portion further comprises a non-transitory memory, and wherein the auditory prompt set associated with the releasable housing portion is stored on the non-transitory memory of the releasable housing portion.

6. The system of claim 1 wherein the auditory prompt set associated with the releasable housing portion is stored on a server system, and wherein the non-transitory memory further comprises instructions to retrieve the auditory prompt set from the server system.

7. The system of claim 1 wherein the control unit further comprises a speech unit and wherein the instructions to output the active prompt set comprise instructions to transmit a signal associated with the active prompt set from the speech unit to the speaker.

8. The system of claim 1 wherein the analyte measurement device further comprises a display.

9. The system of claim 1 wherein the analyte measurement device further comprises a microphone.

10. The system of claim 1 wherein the analyte measurement device is configured to collect and analyze a plurality of fluid samples.

11. The system of claim 1 wherein the system further comprises a cartridge containing a plurality of analyte quantification members.

12. The system of claim 1 wherein the releasable housing portion comprises at least one of a front cover, a back cover, and a battery cover.

13. The system of claim 1 wherein the non-transitory memory comprises instructions to detect the information transmitter and set the auditory prompt set associated with the detected information transmitter as the active prompt set automatically.

14. The system of claim 1 wherein the information transmitter comprises a chip configured to wirelessly communicate with the control unit.

15. The system of claim 1 wherein the information transmitter comprises a USB device.

16. The system of claim 1 wherein the instructions to detect the information transmitter comprise instructions to detect an electrical connection between the analyte measurement device and the information transmitter.

17. The system of claim 1 wherein the instructions to detect the information transmitter comprise instructions to detect physical contact between the analyte measurement device and the information transmitter.

18. A system comprising:
an analyte quantification member configured to react with an analyte in a fluid sample to produce a measureable response; and
an analyte measurement device configured to detect the measureable response and determine a concentration of the analyte, wherein the analyte measurement device comprises:
a housing;
a speaker disposed within the housing; and
a control unit disposed within the housing, wherein the control unit comprises:
a non-transitory memory comprising instructions to output an auditory prompt set via the speaker, wherein the auditory prompt set comprises an alert that warns a user of an impending lance with a skin penetration member by indicating an expiring time period until the lance occurs, and an alert that the analyte measurement device has acquired a usable sample; and
a processor programmed to carry out the instructions on the non-transitory memory.

19. The system of claim 18 wherein the auditory prompt set is stored on the non-transitory memory.

20. The system of claim 18 wherein the auditory prompt set is stored on a server system, and wherein the non-transitory memory further comprises instructions to retrieve the auditory prompt set from the server system.

21. The system of claim 18 wherein the control unit further comprises a speech unit and wherein the instructions to output the auditory prompt set comprise instructions to transmit a signal associated with the auditory prompt set from the speech unit to the speaker.

22. The system of claim 18 wherein the analyte measurement device further comprises a microphone.

23. The system of claim 18 wherein the analyte measurement device is configured to collect and analyze a plurality of fluid samples.

24. The system of claim 18 wherein the system further comprises a cartridge containing a plurality of analyte quantification members.

25. The system of claim 18 wherein the auditory prompt set further comprises an instruction to position a sampling site relative to a test port of the analyte measurement device.

26. The system of claim 18 wherein the auditory prompt set further comprises an alert that the concentration of the analyte in the fluid sample has been obtained.

27. The system of claim 18 wherein the auditory prompt set comprises an instruction to apply additional sample to the analyte measurement device.

28. The system of claim 18 wherein the non-transitory memory further comprises instructions to output the auditory prompt set via the speaker in response to a single action taken by the user.

29. The system of claim 28 wherein the single action taken by the user is initiating an analyte measurement operation.

30. The system of claim 18 wherein the analyte measurement device further comprises a display.

31. The system of claim 30 wherein the non-transitory memory further comprises instructions to output the auditory prompt set and a visual prompt set on the display simultaneously.

32. The system of claim 31 wherein the visual prompt set comprises a graphical representation of one or more steps of a sampling process.

* * * * *